(12) United States Patent
Subhadra

(10) Patent No.: US 10,119,116 B2
(45) Date of Patent: Nov. 6, 2018

(54) DEVICES, SYSTEMS AND METHODS FOR THE PRODUCTION OF HUMANIZED GUT COMMENSAL MICROBIOTA

(71) Applicant: Bobban Subhadra, Sarasota, FL (US)

(72) Inventor: Bobban Subhadra, Sarasota, FL (US)

( * ) Notice: Subject to any disclaimer, the term of this patent is extended or adjusted under 35 U.S.C. 154(b) by 0 days.

(21) Appl. No.: 15/470,214

(22) Filed: Mar. 27, 2017

(65) Prior Publication Data

US 2018/0030404 A1 Feb. 1, 2018

Related U.S. Application Data

(62) Division of application No. 15/221,927, filed on Jul. 28, 2016, now abandoned.

(51) Int. Cl.

| | | |
|---|---|---|
| *C12N 1/20* | (2006.01) | |
| *C12M 3/00* | (2006.01) | |
| *A61K 9/00* | (2006.01) | |
| *A61K 35/74* | (2015.01) | |
| *C12N 7/00* | (2006.01) | |
| *C12N 1/04* | (2006.01) | |
| *C12M 1/34* | (2006.01) | |
| *C12M 1/00* | (2006.01) | |
| *C12M 1/12* | (2006.01) | |
| *A61K 35/00* | (2006.01) | |

(52) U.S. Cl.
CPC .............. *C12N 1/20* (2013.01); *A61K 9/0031* (2013.01); *A61K 9/0053* (2013.01); *A61K 35/74* (2013.01); *C12M 23/02* (2013.01); *C12M 23/06* (2013.01); *C12M 23/20* (2013.01); *C12M 23/42* (2013.01); *C12M 25/10* (2013.01); *C12M 41/12* (2013.01); *C12M 41/14* (2013.01); *C12M 41/34* (2013.01); *C12N 1/04* (2013.01); *C12N 7/00* (2013.01); *A61K 2035/11* (2013.01); *C12N 2795/00032* (2013.01); *C12N 2795/00051* (2013.01)

(58) Field of Classification Search
None
See application file for complete search history.

(56) References Cited

U.S. PATENT DOCUMENTS

| | | |
|---|---|---|
| 4,789,634 A | 12/1988 | Miller-Lierheim |
| 5,266,476 A | 11/1993 | Sussman |
| 6,379,619 B1 | 4/2002 | Rozga |
| 9,040,101 B2 | 5/2015 | Heiman |
| 9,060,540 B2 | 6/2015 | Rochat |
| 9,113,653 B2 | 8/2015 | Maranz |
| 9,131,721 B2 | 9/2015 | Rochat |
| 9,173,910 B2 | 11/2015 | Kaplan |
| 9,192,179 B2 | 11/2015 | Zamzam |
| 9,192,361 B2 | 11/2015 | Stevens |
| 9,215,997 B2 | 12/2015 | Shuck |
| 2002/0009436 A1 | 1/2002 | Doyle |
| 2004/0023360 A1 | 2/2004 | Lacroix |
| 2004/0132164 A1 | 7/2004 | Doyle |
| 2005/0239706 A1 | 10/2005 | Backhed |
| 2007/0036836 A1 | 2/2007 | Faure |
| 2007/0196890 A1 | 8/2007 | Vulevic |
| 2008/0102162 A1 | 5/2008 | Delcour |
| 2008/0261916 A1 | 10/2008 | Csaba |
| 2008/0274127 A1 | 11/2008 | Faure |
| 2009/0142842 A1 | 6/2009 | Yockman |
| 2009/0143414 A1 | 6/2009 | Kume |
| 2009/0170141 A1 | 7/2009 | Brown |
| 2010/0048595 A1 | 2/2010 | Gordon |
| 2010/0068779 A1 | 3/2010 | Wells |
| 2010/0086527 A1 | 4/2010 | Huber-Haag |
| 2010/0086955 A1 | 4/2010 | Harran |
| 2010/0129816 A1 | 5/2010 | Maria |
| 2010/0172874 A1 | 7/2010 | Turnbaugh |
| 2010/0254949 A1 | 10/2010 | Barboza |
| 2010/0317573 A1 | 12/2010 | Goedhart |
| 2011/0009359 A1 | 1/2011 | Amor |
| 2011/0034407 A1 | 2/2011 | Ferdinand |
| 2011/0123504 A1 | 5/2011 | Brandt |
| 2011/0124078 A1 | 5/2011 | Edwards |
| 2011/0280840 A1 | 11/2011 | Blaser |
| 2012/0027724 A1 | 2/2012 | Brinkmann |
| 2012/0058094 A1 | 3/2012 | Blaser |
| 2012/0135957 A1 | 5/2012 | Dugenet |
| 2014/0045744 A1 | 2/2014 | Gordon |
| 2014/0147417 A1 | 5/2014 | Sadowsky |
| 2014/0286920 A1 | 9/2014 | Mayra-Makinen |
| 2015/0050725 A1 | 2/2015 | Pieczarek |
| 2015/0110834 A1 | 4/2015 | Underhill |
| 2015/0297642 A1 | 10/2015 | Borody |
| 2015/0376697 A1 | 12/2015 | Li |

FOREIGN PATENT DOCUMENTS

| | | |
|---|---|---|
| CN | 101368154 A | 2/2009 |
| WO | 2008076696 | 6/2008 |

(Continued)

OTHER PUBLICATIONS

Barnea, et al., Obesity and Metabolic Disease After Childhood Cancer, Oncology (Williston Park). 29(11):849-55 (2015).

(Continued)

*Primary Examiner* — Robert J Yamasaki
(74) *Attorney, Agent, or Firm* — Smith, Gambrell & Russell, LLP; Charles Vorndran

(57) ABSTRACT

One embodiment provides a commensal gut production platform for ex vivo production of human gut commensal microbiota. Another embodiment provides devices, systems and methods for ex vivo culturing of gut microflora in a system that mimics the human gut environment. The culturing of the commensal microbiota in the disclosed systems produces gut microbiota having defined characteristics and properties that can be exploited to treat various conditions in a subject.

15 Claims, 7 Drawing Sheets

Specification includes a Sequence Listing.

(56) References Cited

FOREIGN PATENT DOCUMENTS

| WO | 2010002890 | 1/2010 | | |
|---|---|---|---|---|
| WO | 2010151842 | 12/2010 | | |
| WO | 2011022660 | 2/2011 | | |
| WO | 2011103123 | 8/2011 | | |
| WO | 2011107482 | 1/2012 | | |
| WO | 2012024638 | 2/2012 | | |
| WO | 2014193980 | 12/2014 | | |
| WO | 2015189472 | 12/2015 | | |
| WO | 2015200842 | 12/2015 | | |
| WO | 2015200901 | 12/2015 | | |
| WO | WO-2016170285 A1 * | 10/2016 | ............ | A61K 35/38 |
| WO | WO-2017131839 A2 * | 8/2017 | ............ | C12M 23/16 |

OTHER PUBLICATIONS

Di Cerbo, et al., Mechanisms and therapeutic effectiveness of lactobacilli, J Clin Pathol., 69(3):187-203 (2015).

Ladas, et al., The safety and feasibility of probiotics in children and adolescents undergoing hematopoietic cell transplantation, Bone Marrow Transplant., 51 (2):262-6 (2015).

Larson, et al., Human serum amyloid A3 peptide enhances intestinal MUC3 expression and inhibits EPEC adherence, Biochem Biophys Res Commun.,300 (2):531-40 (2003).

Li, et al., The influence of gut microbiota on drug metabolism and toxicity, Expert Opin Drug Metab Toxicol., 12 (1):31-40 (2015).

McGarr, et al., Diet, anaerobic bacterial metabolism, and colon cancer: a review of the literature, J Clin Gastroenterol., 39(2):98 109 (2005).

Mitra, et al., Cervical intraepithelial neoplasia disease progression is associated with increased vaginalmicrobiome diversity, Sci Rep., Nov. 17;5:16865 (2015).

Patel, et al.,, Probiotic Bacteria Induce Maturation of Intestinal Claudin 3 Expression and Barrier Function, Am J Pathol., 180(2):626 35 (2012).

Ridlon and Bajaj, The human gut sterolbiome: bile acid-microbiome endocrine aspects and therapeutics, Acta Pharm Sin B., 5(2):99-105 (2015).

Taur, et al., Role of intestinal microbiota in transplantation outcomes, Best Pract Res Clin Haematol., ;28(2-3): 155-161 (2015).

Torres, et al., Characterization of the salivary microbiome in patients with pancreatic cancer,. PeerJ., Nov. 5;3:e1373 (2015).

Vetizou, et al.., Anticancer immunotherapy by CTLA-4 blockade relies on the gut microbiota, Science, 350(6264): 1079 1084 (2015).

Everard, et al., "Cross-Talk Between Akkermansia Muciniphila and Intestinal Epithelium Controls Diet-Induced Obesity", Proc Natl Acad Sci USA, pp. 110(22): 9066-71 (2013).

Sokol, et al., "Faecalibacterium Prausnitzii is an Anti-Inflammatory Commensal Bacterium Identified by Gut Microbiota Analysis of Crohn Disease Patients", Proc Natl Acad Sci USA, pp. 105(43): 16731-6 (2008).

U.S. Appl. No. 15/221,927 entitled "Devices, Systems and Methods for the Production of Humanized Gut Commensal Microbiota" filed Jul. 28, 2016.

* cited by examiner

Thin layer Glass wool sheet — A

High-perforated high-surface area rough sponge — B

DEVICES, SYSTEMS AND METHODS FOR THE PRODUCTION OF HUMANIZED GUT COMMENSAL MICROBIOTA

FIELD OF THE INVENTION

The present invention generally relates to the ex vivo production of gut microbiota and more particularly in a humanized commensal form that can be used for a variety of purposes such as therapeutics, diagnostics, and a research tool.

REFERENCE TO A SEQUENCE LISTING

The Sequence Listing submitted on May 25, 2017, as a text file named "064472001DIVseqlisting.txt" created on May 24, 2017, and having a size of 719 bytes is hereby incorporated by reference pursuant to 37 C.F.R. § 1.52(e)(5).

BACKGROUND OF THE INVENTION

The human microbiota is the aggregate of microorganisms that resides on the surface and in deep layers of skin, in the saliva and oral mucosa, in the conjunctiva, and in the gastrointestinal tracts, and the human microbiome refers to their genomes. The human body consisting of about 100 trillion cells and carries about ten times as many microorganisms in the intestines. It is estimated that these gut flora have around 100 times as many genes in aggregate as there are in the human genome. Indeed, by cell count, humans are 10% human and 90% bacterial flora. The microbiome is reckoned to have around 3 million functional genes compared to 23,000 genes in human beings. The far larger genome of the microbiome has correspondingly greater capabilities in modulating human health and well-being.

Research suggests that the relationship between gut flora and humans is not merely commensal (a non-harmful coexistence), but rather a symbiotic relationship. These microorganisms perform a host of useful functions, such as fermenting unused energy substrates, training the immune system, forming a protective mucosal biofilm, preventing growth of harmful, pathogenic bacteria, regulating the development of the gut, producing vitamins for the host (e.g., biotin and vitamin K), producing hormones to direct the host to store fats, producing signaling molecules that promote homeostasis, metabolizing drugs, xenobiotics, and the like.

Collectively, human microbiota and microbiome play vital roles in body metabolism, immune system, and intestinal homeostasis. The human microbiome is now considered as fully functional additional organ—a highly adaptable and organized—with key functions for the body development and health. The microbiota are considered to have the characteristics of organogenesis after birth, anatomy, physiology, pathology, and other features. The health and diversity of human microbiota are becoming more and more important in medical research for treating autoimmune, infectious, and metabolic diseases. For example, the gut microbiota has the potential for being mal-developed or being infested with various parasites, viruses, fungi or bacteria. Hence, treatments for such an unhealthy conditions are needed.

Invasion of the microbiota by pathogens can constitute various illnesses such as Irritable Bowel Syndrome (IBS), *C. difficile* infection (CDI), diarrhea, pseudomembranous colitis and others. A common underlying factor shared by all such disorders is that their onset is after some extraneous invading infection, albeit the patients may not remember this as it might have occurred decades before, for example, as with IBS or constipation.

Dysbiosis of the GI microbiota is associated with many disease susceptibilities, including obesity, steatosis, diabetes, atherosclerosis malignancy, liver disease and GI pathology such as inflammatory bowel disease (IBD). It is clear that there is direct and indirect crosstalk between this microbial community and host immune response. However, the precise mechanism of this microbial influence in disease pathogenesis remains elusive and is now a major research focus.

There has recently been a massive development in our knowledge of bowel flora related conditions. Some of these conditions are easily understandable and are caused by abnormal bacteria e.g., *Salmonella enteritis*. Other conditions such as obesity are more difficult to comprehend in terms of the mechanisms that might be playing a role in the causality of obesity yet originating in the bowel flora. Nonetheless, there is a growing list of various conditions that are now becoming tied to the microbiota. It is now recognized that conditions such as type 1 diabetes (T1D) and IBS, Colitis, Crohn's Disease, constipation, Metabolic Syndrome, IBD to name a few, have clear and increasing evidence that changes in the microbiota are associated with some of these conditions.

In the past, various pharmacotherapeutic principles have been tried with limitations. In addition, because of undesirable side effects, the Food and Drug Administration (FDA) has had to recall several obesity drugs from the market. Those that are approved also have side effects. Currently, two FDA-approved anti-obesity drugs are orlistat, a lipase inhibitor, and sibutramine, a serotonin reuptake inhibitor. Orlistat acts by blocking the absorption of fat into the body. An unpleasant side effect with orlistat, however, is the passage of undigested oily fat from the body. Sibutramine is an appetite suppressant that acts by altering brain levels of serotonin. In the process, it also causes elevation of blood pressure and an increase in heart rate. Other appetite suppressants, such as amphetamine derivatives, are highly addictive and have the potential for abuse. Moreover, different subjects respond differently and unpredictably to weight-loss medications.

Traditionally, for infections, antibiotics can give transient improvement, but often fail (for example, recurrent CDI), and these failures point-to a need for a fresh approach to treatment. Apart from antibiotics and as with other organs, transplantation is also one possible treatment. For transplantation, in many instances the infection cannot be demonstrated by culture as the diversity of microbial sub-species level composition is quite enormous, and only a small percentage of these can be cultured.

Fecal Microbiota Transplantation (FMT) previously known as "Fecal Bacteriotherapy" (see, e.g., Borody (2004) J. Clin. Gast. 38:475-483) represents a therapeutic method which allows the most rapid reconstitution of the normal composition of colonic microbial communities. It has been a therapy of last resort for patients with severe CDI and particularly with relapsing CDI. FMT is now becoming much more accepted medically; however, there is a need to improve on the deficiencies of FMT-based therapeutics. While there is wide availability of good donor FMT material, design of a complex yet clinically active composition that is patient-acceptable, e.g., not resemble crude, smelling stool, but rather a more acceptable pharmaceutical-like 'biological' composition that will gain wider patient and physician acceptance, is needed.

There is a need for clinically active FMT compositions that are more acceptable to a wide patient and physician group. There is a need for clinically active FMT in fields where patients are not desperately ill (where acceptance is quite high). Implantation (e.g., transplantation) of crude homogenized human stool has abolished CDI, and the donor flora implants for prolonged periods of time, see, e.g., Grehan (2010) J. Clin. Gastroenterol. 44(8):551-561, Thus, it is an object of the invention to provide devices and systems for culturing and expanding gut commensal microbiota.

It is another object of the invention to provide compositions and methods for treating disease or pathologies of the human gastrointestinal tract using cultured gut commensal microbiota.

SUMMARY OF THE INVENTION

One embodiment provides a commensal gut production platform for ex vivo production of human gut commensal microbiota. Another embodiment provides devices, systems and methods for ex vivo culturing of gut microflora in a system that mimics the human gut environment. The culturing of the commensal microbiota in the disclosed systems produces gut microbiota having defined characteristics and properties that can be exploited to treat various conditions in a subject.

An exemplary device and system for culturing humanized commensal gut microbiota includes an airtight gas system equipped with a system to supply and/or monitor gases, a humidifying system to maintain high humidity inside the airtight anaerobic gas system, a column system made from a plurality of columns connected in a tortious manner, a plurality of cartridges to provide substrate for commensal microbiota adhesion, growth and proliferation, and a temperature regulation system to regulate the temperature inside the apparatus. In one embodiment the cartridges are removable.

In another embodiment, the system contains a functional screening portal. The functional screening portal includes a substrate to grow various live human cell types in monolayer or as tissue scaffold or 3-D printed vascularized tissue scaffolds. Exemplary cells include but are not limited to immune cells, enterocytes, colonocytes, lymphocytes, hepatocytes, glial cells, neurons, and keratinocytes. The functional screening portal has a separate gas line to provide the optimum gaseous mixture for the cell growth. In one embodiment, the screening portal 110 is in fluid communication with a column cartridge 104 so that metabolites from the column cartridges can diffuse into the screening portal and the effect of microbiota metabolites on various function of various tissue systems (e.g., cell signaling, cell proliferation, apoptosis and other cellular bioactivity) can be studied. The functional screening portal has a membrane with 0.2-0.4 um pores separating the cells from the microbiota column (FIGS. 7A).

An exemplary method for producing humanized commensal gut microbiota includes screening stool and optionally serum samples from a healthy human donor, collecting, screening, purifying, and selecting microbiota samples from the healthy human donor, mixing the selected microbiota samples with a medium to prepare a seed culture, infusing the seed culture into the cartridge for culturing and further processing in the system.

In one embodiment, the microbiota are screened for secreting anti-cancer agents, anti-inflammatory agents, anti-viral agents or combinations thereof.

Methods for treating gastrointestinal illnesses are provided in which human commensal microbiota are cultured ex vivo, harvested, and administered to a subject in need thereof.

Other and further aspects and features of the present disclosure will become readily apparent to those skilled in the art from the following detailed description wherein embodiments of the present disclosure are described simply by way of illustration of one of the several modes contemplated to carry out the present disclosure. As will be realized, the present disclosure is capable of other and different embodiments, and its several details are capable of modifications in various obvious respects, all without departing from the present disclosure. Accordingly, the drawings and description are to be regarded as illustrative in nature, and not as restrictive.

BRIEF DESCRIPTION OF THE DRAWINGS

FIG. 2A shows a column 102 having an interior with villi-like projections on loose glass wool. FIG. 2B shows a column 102 having an interior containing a glass wool substrate. FIG. 2C shows a column 102 having an interior having brush-like cartridges with glass wool. FIG. 2D shows a column having an interior containing a highly porous sponge.

FIG. 5A shows glass wool. FIG. 5B shows the substrate can be a perforated sponge. FIG. 5C shows the substrate can be a high surface area porous glass wool.

DETAILED DESCRIPTION OF THE INVENTION

I. Definitions

Figure 1:
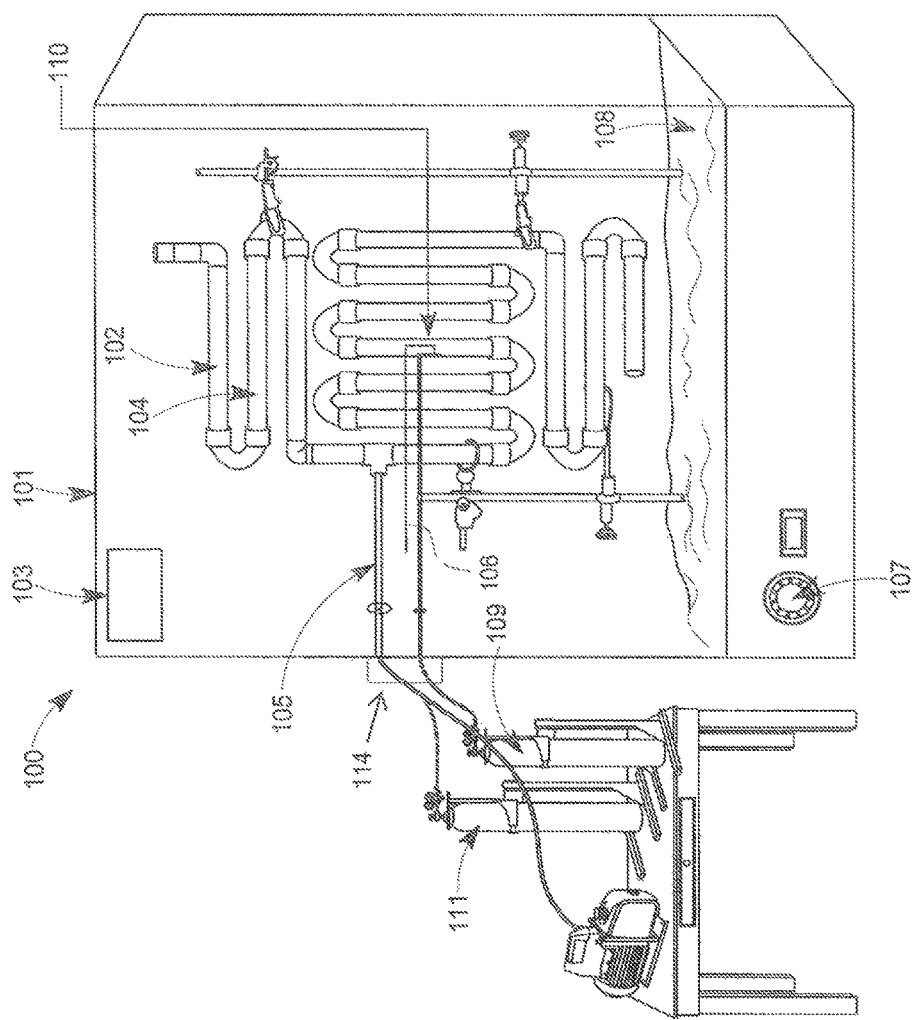
FIG. 1 represents an exemplary commensal microbiota producing system 100.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "coupled" is defined as connected, whether directly or indirectly through intervening components, and is not necessarily limited to physical connections. The connection can be such that the objects are permanently connected or connected in a releasable manner.

As used herein, the term "inside" indicates that at least a portion of a region is partially contained within a boundary formed by the object. As used herein, the term "comprising," when utilized, means "including, but not necessarily limited to"; it specifically indicates open-ended inclusion or membership in the so-described combination, group, series and the like.

Other Definitions

The term "microbiota" refers to the ecological community of commensal, symbiotic and pathogenic microorganisms that share a host's body space.

The term "microbiome" refers, collectively, to the collection of microbial genomes in an environment.

The term "commensal" refers to organisms that are normally harmless to a host, and can also establish mutualistic relations with the host. The human body contains about 100 trillion commensal organisms, which have been suggested to outnumber human cells by a factor to 10.

The term "microbial derived component" refers to a component consisting of, emanating from, or produced by members of the microbiota. The component can be, for example, a microbe, a microbial protein, a microbial secretion, or a microbial fraction.

The term "modulating" as used in the phrase "modulating a microbial niche" is to be construed in its broadest interpretation to mean a change in the representation of microbes in a bacterial niche of a subject. The change may be an increase or a decrease in the presence of a particular species, genus, family, order, class, or phylum. The change may also be an increase or a decrease in the activity of an organism or a component of an organism, such as a bacterial enzyme, a bacterial antigen, a bacterial signaling molecule, or a bacterial metabolite.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

II. Devices for Production of Humanized Commensal Gut Microbiome/Microbiota

Devices and methods for the production of humanized commensal gut microbiota which is capable of being used for various medical and research purposes are provided. The devices and methods relate to production of humanized gut commensal flora having the characteristics of human gut commensal microbiota produced in vivo. One embodiment provides an apparatus that has predictable and quality controlled flora for the production of humanized gut commensal microbiota. The disclosed devices can be used to determine the antibiotic resistance gene profile of the flora and provide superior microbiota production and adherence properties.

FIG. 1 illustrates the design various components of an exemplary system for the production of humanized commensal gut microbiome capable of being used for the various medical and research purposes. The system includes an apparatus 100, wherein the apparatus 100 includes an airtight gas system 103 with its outside boundary 101 that provides the required environment to facilitate growth of obligate anaerobic gut commensal microorganisms for the production of humanized commensal gut microbiome/microbiota. The suitability of environment for the production of humanized commensal gut microbiota plays an important role and without it the production is hampered. The airtight gas system 103 includes a gas control/vacuum control system 105-106 to supply and/or monitor gases. The gas control/vacuum control system 105-106 controls the flow of gas with respect to quantity and intervals for flow. The gas control/vacuum control system 105-106 helps the apparatus 100 to create a suitable environment for the growth and production of the humanized commensal gut microbiota. The system also includes a gas monitor device 114 such as an oxygen monitor, carbon dioxide monitor, nitrogen monitor or a combination thereof. The gas control/vacuum control system 105-106 provides a means for supplying and/or monitoring of oxygen, nitrogen, carbon dioxide, and other gases. The gas control/vacuum control system 105-106 is capable of supplying the required amount of any particular gas or combination of gases into the system for the growth and production of the humanized commensal gut microbiome. For example, the gas control system 105-106 can supply oxygen, carbon dioxide and combinations thereof. The airtight gas system also includes a humidifying system 108, to maintain high humidity inside the airtight gas system 103.

In one embodiment, the device is an airtight-system but not a complete or obligate anaerobic system, but rather a gaseous gradient system to re-create/mimic the gas gradient of the human enteric system. For example, in the resting state there are usually about 200 ml of gas in the human gastrointestinal tract. Its composition varies: between 20-90 percent is nitrogen, up to 10 percent is oxygen, up to 50 percent is hydrogen, up to 10 percent is methane, and between 10 and 30 percent is carbon dioxide. The measured partial oxygen pressure ($pO_2$) levels ranged from 58 mmHg in the human stomach to 3 mmHg near the distal sigmoid colon.

The systems for creating gas gradients in the current device includes: 1) injecting gas gradients into the cartridge; 2) taking out excess air by anaerobic unit (palladium catalyst unit; and) 3) simultaneous injection of oxic (21% oxygen) or anoxic (0.1%) culture media. These built-in techniques allow the establishment and maintenance of an oxygen gradient representative of the in vivo situation. Oxygen sensors allow continuous monitoring of the dissolved oxygen concentrations in the chamber. The measured dissolved oxygen concentrations in the screening portal chamber is stabilized to 5.5% which is comparable to the actual recorded concentrations in various human tissues, that is, 4.6%. The oxygen concentration in the humanized microbial growing cartridge chamber ranged from 0.8-2.6% of dissolved oxygen. These established anoxic conditions are analogous to those observed in vivo between the mucus layer and the luminal anaerobic zone (0.88%) and such oxygen concentrations have been reported to be favorable for the growth of diverse microbiota, including obligate anaerobes. The gradient of oxygen in the growing unit is maintained through the continuous perfusion of gas mixture, anoxic media (0.1%) into the microbial microchamber and further shaped by the consumption of oxygen and various gases by the complex microbiota in the growing unit. A luminal oxygen gradient might play a role in "aerotaxis" of motile bacteria, through bacterial energy sensing pathways, into the mucus layer where they are able to survive and proliferate. This resembles the ecology of environmental microoxygenic zones, such as activated sewage sludge, marine snow and soil aggregates that develop oxygen gradients, whereby microbes juxtaposed to the oxygenated environment consume oxygen before it reaches the interior of the microbial community. The presence of a spatial gradient of oxygen in the lumen provides an explanation for the enrichment of aerobic and facultative anaerobic organisms from the Proteobacteria and Actinobacteria phyla in rectal biopsy and swab samples. The gas gradient is maintained to be 0.8-2.0% oxygen or 2-60 mm Hg in the system and is tunable.

The apparatus further includes a column system, the column system having a plurality of columns 102 connected together in tortious manner, for example a zig zag manner. The plurality of columns 102 are hollow cylindrical tubes made from a durable material such as plastic, polymeric material, or metal. Any suitable material can be used for making the columns. The plurality of columns 102 is detachably connected at the edges with the help of connectors. The hollow column preset in the system plays an important role in production of the humanized commensal gut microbiota in order to provide accurate and required growth. The plurality of columns are packed with growth substrates such as but not limited to glass wool, perforated sponge and the like.

The apparatus includes a plurality of cartridges 104, to provide substrate for the adhesion, growth and proliferation of commensal microorganisms. The pluralities of cartridges 104 as defined in the apparatus have villi like micro projections with crypts that mimic the human inner gut lining.

The cartridges 104 are filled with suitable materials which provide required growth environment and media for the human gut. Further, the plurality of cartridges is coated with extracellular matrix proteins to enhance and support the production of the humanized commensal gut microbiome. Subsequent to the filling of suitable materials and covering the cartridges with extracellular matrix proteins, the cartridges are seeded with live cells of the gastrointestinal system. The cells of the gastrointestinal system seeded into the cartridges are the cells which will be used for the production of the humanized commensal gut microbiota. After seeding the cartridges with human gut microbiota, the cartridges are loaded into the column 102 and assembled inside the airtight chamber 103 for production.

Figures 2A, 2B, 2C, 2D:
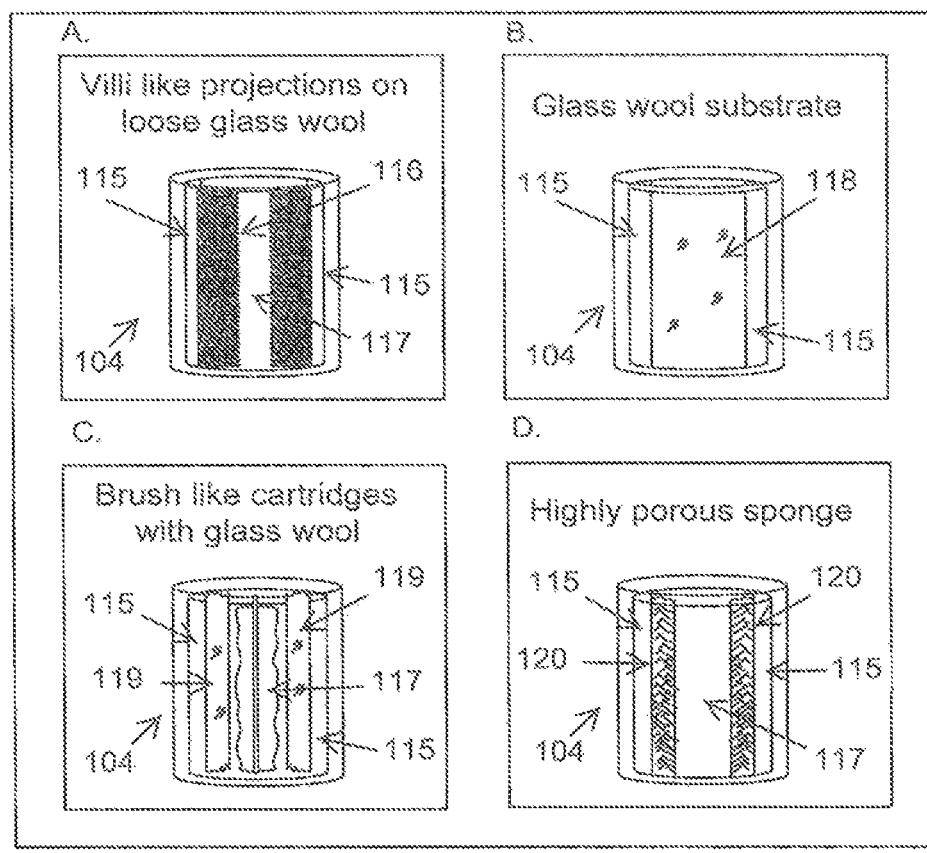
FIGS. 2A-2D represents the inset of different types of interiors for columns 102.

FIGS. 2A-2D illustrate various non-limiting examples of villi like projections as defined for substrate cartridges 104, on loose glass wool, glass wool substrate, brush like cartridges with glass wool and highly porous sponge. FIG. 2A shows the cross section of an exemplary cartridge 104 that contains an inner layer 115 in contact with the inner surface of cartridge 104. First layer 115 contains a layer of extracellular matrix proteins coating the interior surface of cartridge 104 and a layer of human intestine cells covering the layer of extracellular matrix proteins. A secondary substrate is in contact cells. In FIG. 2a the secondary substrate is loose glass wool with villi-like projections in the lumen 117. In certain embodiment, cartridge 104 has a secondary substrate that comply fills the interior of cartridge 104 so there is no lumen 117. FIG. 2B shows the cross section of another cartridge 104 in which the interior of the cartridge is filled with glass wool substrate 118. FIG. 2C is another embodiment of cartridge 104 in which the secondary substrate is brush-like glass wool. This cartridge optionally contains a lumen 117. FIG. 2D shows another embodiment of cartridge 104 in which the secondary substrate is highly porous sponge with an optional lumen 117.

In some embodiments, secondary substrate is coated with extracellular matrix proteins, mucin proteins or commensal colonizing factors.

The apparatus for the production of humanized commensal gut microbiota includes an integrated anaerobic atmosphere generating means for generating an anaerobic atmosphere for the apparatus which create an ambient environment for the production of humanized commensal gut microbiota. Further the anaerobic generating means comprise provisions such as but not limited to gas-pak, oxygen removing catalyst, and gas infusion lines. The anaerobic atmosphere maintenance is aided by the gas control/vacuum control system 105-106 which provides nitrogen gas through a Nitrogen gas cylinder 111, Oxygen and Carbon Dioxide through Oxygen+$CO_2$ cylinder 109 and several other appropriate means that will be apparent to those skilled in the art for supplying and/or monitoring other gases.

The apparatus also includes a temperature regulation system 107 to regulate the temperature inside the apparatus 100, which is essential to maintain the optimum growth conditions for the cultured microbiota. Temperature regulation system 107 includes a temperature sensor with a thermostat-driven heater mechanism to maintain the temperature inside the chamber to be 35-37° C.

Figure 7A:
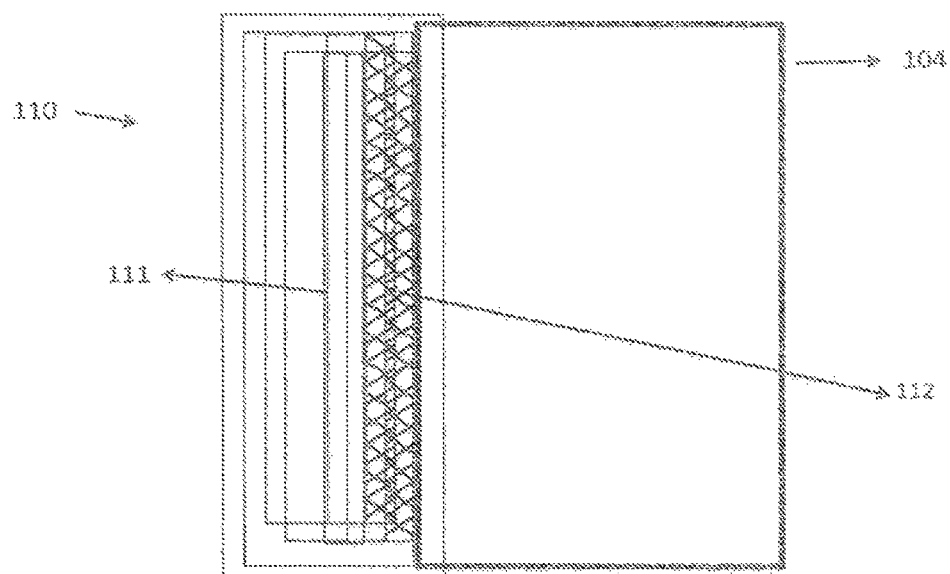
FIGS. 7A and 7B show an exemplary screening portal 110.
Figure 7B:
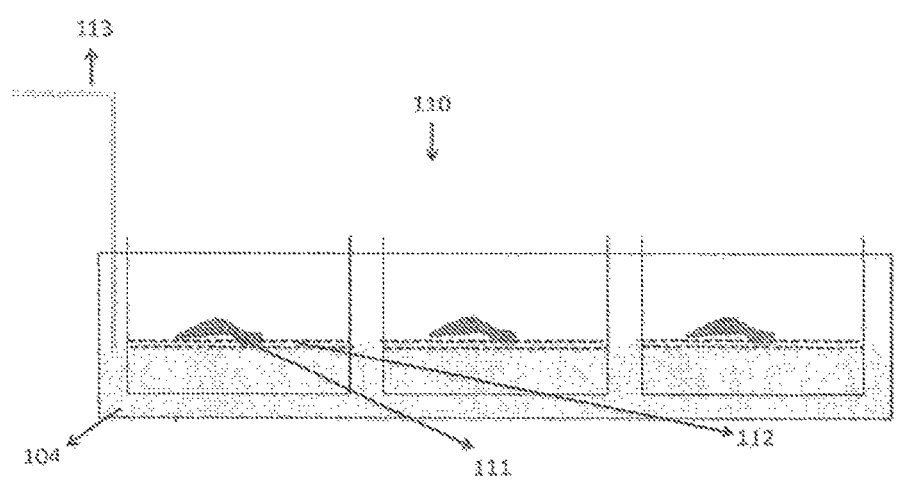

The apparatus also includes a functional screening portal 110 designed for real-time screening of specific activity of a metabolite on different cell types (FIGS. 7A and 7B). The functional screening portal 110 in the apparatus includes a cell-growing surface 111 with cell culture media, and a semi-permeable membrane 112 that allows diffusion of only metabolites.

The functional screening portal 110 is designed to have substrate to grow various live cell types (such as immune cells, enterocytes, colonocytes and the like) and has a membrane separation 112 (0.2-04 µm) from the microbiota column. The functional screening portal 110 has a separate gas line to provide the optimum gaseous mixture, including oxygen for the cell growth. The metabolites from the column cartridges can diffuse into the screening chamber 110 and can be used to study the effect of microbiota metabolites on cell signaling and other cellular bioactivity.

The functional screening portal 110 can also be used to harvest metabolite on a continuous basis to conduct functional studies. The metabolites are drained through a 0.4 um line 113 and stored for various in-vitro assays and models (T-cell maturation, T cell selection, Keratinocyte maturation, Effects on cancer cell line, Re-aggregate tissue scaffold or culture models of various disease models).

Figure 3:
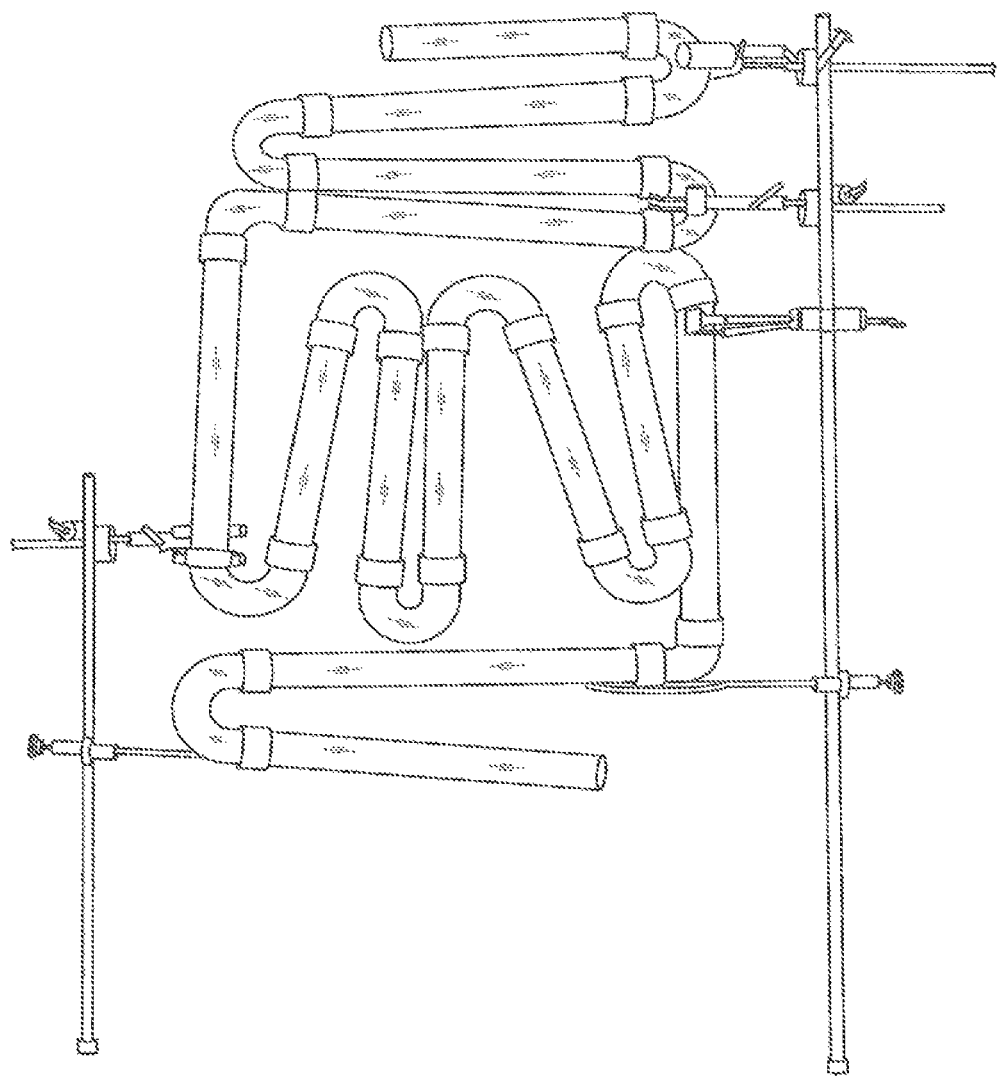
FIG. 3 represents an alternative arrangement of columns 102 in the device without cartridge 104.

FIG. 3 illustrates an exemplary arrangement of the plurality of columns 102 of the column system in a zig zag manner in order to replicate the human gut conditions, prior to loading the cartridges.

Figure 4:
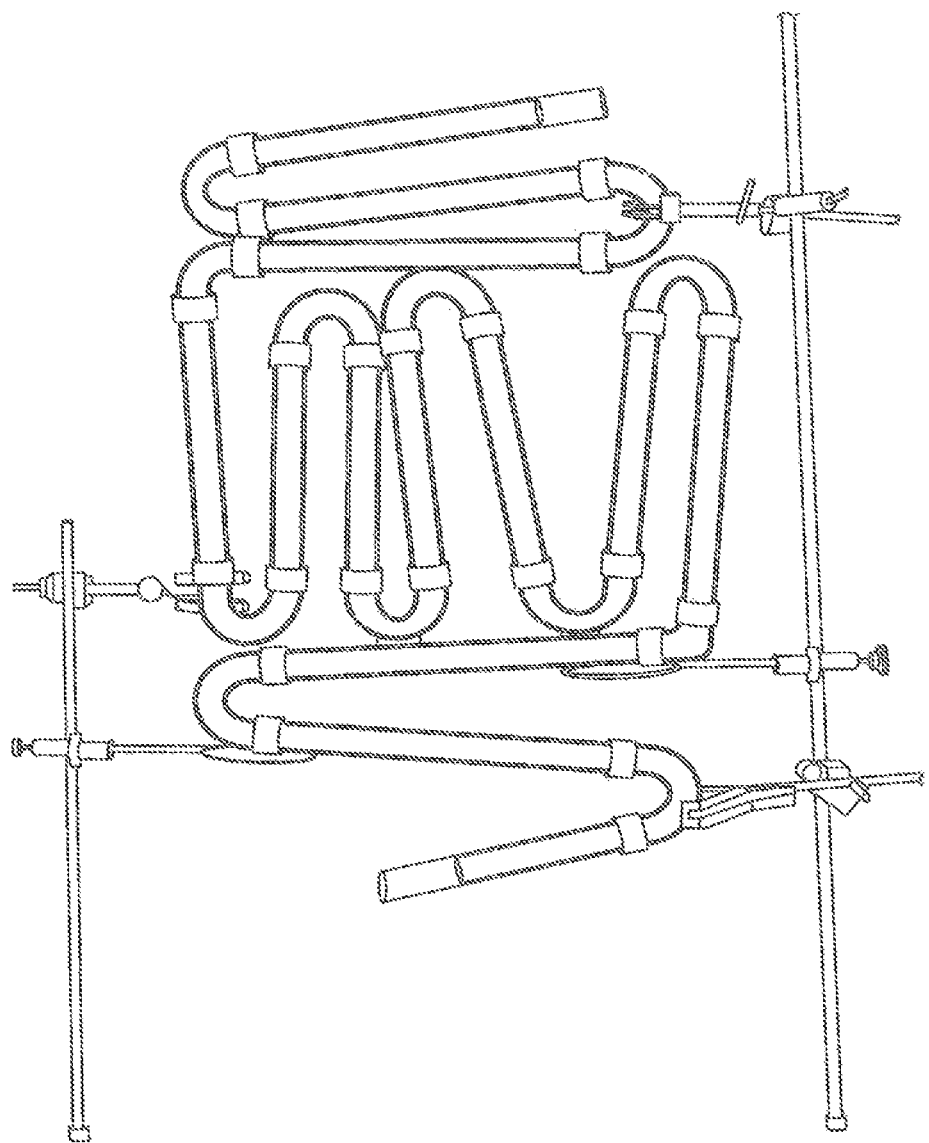
FIG. 4 represents an alternative arrangement of the device with cartridge 104.

FIG. 4 illustrates an exemplary arrangement of the plurality of columns 102 of the column system in a zig zag manner in order to replicate the human gut conditions, with the loaded cartridges.

Figures 5A, 5B, 5C:
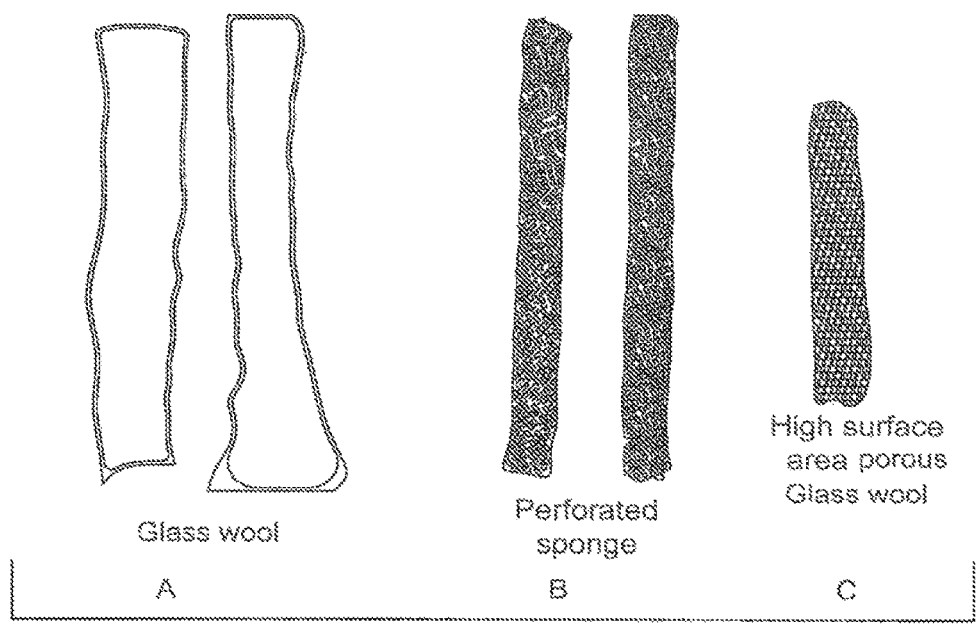
FIGS. 5A-5C show the various growth substrates to be used with the cartridge 104.

FIGS. 5A-5C illustrate the different kinds of substrates that could be used in the apparatus, and can include but not limited to glass wool, perforated sponge and high surface area porous glass wool.

Figure 6A:
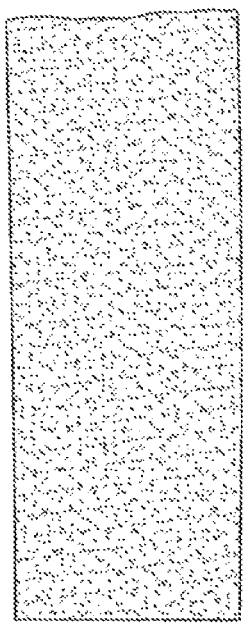
FIGS. 6A and 6B show a section of the thin layer glass wool sheet and high perforated high surface area rough sponge, respectively.
Figure 6B:
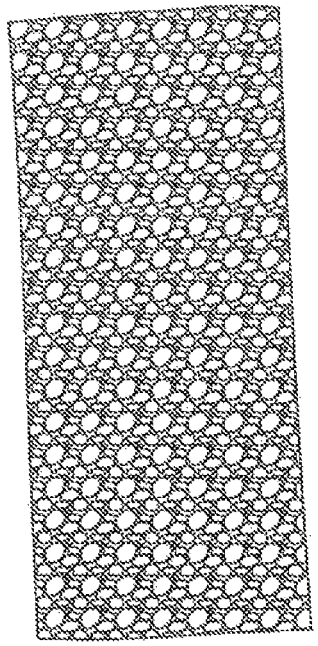

FIG. 6A provides a magnified front view of a thin layer glass wool sheet and FIG. 6B provides a magnified front view of a high perforated high surface area rough sponge.

One embodiment provides an apparatus for the ex vivo production of humanized commensal gut microbiota; wherein the apparatus includes an airtight anaerobic gas system having, a gas control/vacuum control system, to supply and/or monitor gases; a humidifying system, to maintain high humidity inside the airtight anaerobic gas system; a column system, comprising a plurality of columns connected together in a zig zag manner; a plurality of cartridges, to provide substrate for commensal adhesion, growth and proliferation; and a temperature regulation system to regulate the temperature inside the apparatus. In one embodiment, the airtight anaerobic gas system provides the required environment to facilitate growth of obligate anaerobic gut commensals for the production of humanized commensal gut microbiome.

In another embodiment, the gas control/vacuum control system provides a means for supplying and/or monitoring of oxygen, nitrogen, carbon dioxide, and other gases.

In another embodiment the plurality of columns are hollow cylindrical tubes made from plastic or similar material.

In another embodiment the plurality of columns are detachably connected at the edges with the help of connectors.

In another embodiment, the plurality of columns are packet with growth substrates such as but not limited to glass wool, perforated sponge and the like.

In another embodiment, the plurality of cartridges have villi like micro projections with crypts that mimics inner gut lining.

In another embodiment, the plurality of cartridges are coated with extracellular matrix proteins.

In another embodiment, cartridges are further seeded with live cells of intestine.

In another embodiment, the cartridges are loaded into the column and assembled inside the airtight chamber for production.

In another embodiment, the apparatus additionally has an integrated anaerobic generating means.

In another embodiment, the anaerobic generating means comprises provisions such as but not limited to gas-pak, oxygen removing catalyst, and gas infusion lines.

In another embodiment, the apparatus additionally has a functional screening portal designed for real-time screening of specific activity of a metabolite on different cell types.

In another embodiment, the functional screening portal is provisioned with a cell-growing surface with cell culture media, and a semi-permeable membrane that allows diffusion of only metabolites.

In another embodiment, the cartridge to be used in an apparatus for production of humanized commensal gut microbiome includes: a first layer of extracellular matrix proteins, wherein the first layer is coated inside the cartridge; a second layer of cells of intestine, wherein the second layer is seeded on the extracellular matrix proteins; and a packaging layer of a secondary substrate, wherein the packaging layer is coated with adhesive molecules. In one of the preferred embodiment, the first layer of extracellular matrix proteins are collagens, elastins, fibronectins and laminins and the like. In one of the preferred embodiment, the second layer of cells of intestine are live cells, immobilized cells, freeze dried cells and the like.

The secondary substrate of the packaging layer is a highly porous material such as but not limited to glass wool, rockwool, porous sponge, perforated sponge and the like. The cartridge acts as a growth substrate designed to mimic the human gut lining and internal gas pressure of the intestine. Once the cartridges are tightly packed, the secondary substrate creates a gaseous gradient from aerobic to microaerophilic to anaerobic inside the cartridge. For better packaging the adhesive molecules are molecules such as but not limited to collagen, fibrinogen, fibronectin, mucin proteins, commensal colonizing factor proteins and the like.

In another embodiment, the cartridge acts as a growth substrate designed to mimic the human gut lining and internal gas pressure of the intestine.

In another embodiment, the secondary substrate of the packaging layer is a highly porous material such as but not limited to glass wool, rockwool, porous sponge, perforated sponge and the like.

Another embodiment, the secondary substrate after tight packaging creates a gaseous gradient from aerobic to microaerophilic to anaerobic inside the cartridge.

In another, the adhesive molecules are molecules such as but not limited to collagen, fibrinogen, fibronectin, mucin proteins and the like.

In another embodiment, a synthetic media composition for use in culturing humanized commensal gut microbiome includes: organic nitrogen sources, protein sources, carbohydrate sources, metal salts, intestinal secretions, enzymes, vitamins, and trace minerals maintained at a slightly neutral to acidic pH.

In one embodiment, the organic nitrogen source is one or more from hydrolyzed fish extract and/or algae extract, and/or yeast extract.

In one embodiment, the protein source is one or more from peptone and/or amino acids such as L-cysteine and the like.

In one embodiment, the carbohydrate sources are dextrose and soluble starch.

In one embodiment, the metal salts are sodium chloride, potassium phosphate, ammonium citrate, magnesium sulfate, and manganese sulfate.

In one embodiment, the intestinal secretions are primary and secondary bile acids, enzymes, and mucus proteins.

In one embodiment, the synthetic media composition is additionally provided with nutrients and metabolites normally present in the intestine.

In one embodiment, the nutrients and metabolites normally present in the intestine are hydrolyzed amino acids, inulin, oligofructosides, galactofructosides, free fatty acids, triglycerides, gastric juice, pancreatic enzymes, bile acids, and entero-endocrine hormones.

III. Methods of Using the Microbiota Production Systems

A. Ex Vivo Production of Gut Microbiota

The disclosed system has a large number of uses. One embodiment provides methods for the ex vivo production of human gut microbiota. Once a healthy donor is identified, the samples of gut microbiota are collected, screened and purified to remove any impurities present therein such as endotoxins and pathogenic microbes. In one embodiment, the gut microbiota is collected from healthy human volunteers through endoscopy and/or from fecal samples.

The samples are screened properly to detect any defects in the samples, for example inadequate quantities, sample vial integrity, sample contamination etc. The fecal samples are also screened for ova, parasites and the like through stool culture and sensitivity tests. The screening of fecal samples includes tests for *Salmonella, Shigella, Escherichia coli,* O157:H7, *Yersinia enterocolitica, Campylobacter, Clostridium difficile* toxins A and B, *Cryptosporidium* antigen, *Giardia* antigen and the like. The serum samples are screened for diseases such as but not limited to HIV-1, HIV-2, Hepatitis A B C, and the like. Further the serum samples are additionally screened for rapid plasma regain, fluorescent treponemal antibody, and absorbed *Treponema pallidum* and the like. Defective samples are eliminated.

Another embodiment provides a method for the production of humanized commensal gut microbiota including screening stool and serum samples from a healthy human donor; collecting, screening, purifying, and selecting microbiome samples from the healthy human donor; preparation and assembly of a plurality of columns each loaded with a cartridge; mixing of the selected microbiota samples with a media to prepare a seed culture; infusion of the seed culture into the cartridge; and culturing and harvesting the commensal microbiota for further processing.

B. Assembly of the Device

Another embodiment provides a method for the preparation and assembly of a plurality of columns each loaded with a cartridge. The cartridges are loaded into the columns, and then the columns are packed with secondary substrates. After packing the columns with secondary substrates, the loaded and packed columns are assembled, for example in a zig-zag manner through connectors at their edges.

C. Preparation of Synthetic Culture Media

Further, after completion of the screening, purifying of the sample and assembling of the cartridges into the apparatus, the next steps are followed for the ex vivo production of the humanized commensal gut microbiota. The next step includes preparation of a synthetic media, and nutrients and metabolites normally present in the intestine which are infused in the cartridge during culturing. The synthetic media which are infused in cartridge during culturing includes organic nitrogen sources, protein sources, carbohydrate sources, metal salts, intestinal secretions, enzymes, vitamins, and trace minerals maintained at a slightly neutral to acidic pH.

Synthetic media are used because of their known chemical compositions. Synthetic media are useful for nutritional and metabolic studies. The synthetic media may include but is not limited to Czakek's-Dox Medium (GM-9) and Richard's solution (GM-27).

In one embodiment, the synthetic media composition used for culturing humanized commensal gut microbiome includes organic nitrogen sources, protein sources, carbohydrate sources, metal salts, intestinal secretions, enzymes, vitamins, and trace minerals maintained at a slightly neutral to acidic pH. The organic nitrogen source in the synthetic media composition is one or more from hydrolyzed fish extract and/or algae extract, and/or yeast extract. The protein source present in the synthetic media composition for culturing humanized commensal gut microbiome includes one or more from peptone and/or amino acids such as L-cysteine and the like. The carbohydrate sources in the synthetic media composition are dextrose and soluble starch. The metal salts in the synthetic media composition are sodium chloride, potassium phosphate, ammonium citrate, magnesium sulfate, and manganese sulfate. The synthetic media composition includes the intestinal secretions which are preferably primary and secondary bile acids, enzymes, and mucus proteins. The synthetic media composition possesses slightly neutral to acidic pH is around 6.8.

Further the synthetic media composition includes additional nutrients and metabolites normally present in intestine. The synthetic media includes nutrients and metabolites that are normally present in intestine are hydrolyzed amino acids, inulin, oligofructosides, galactofructosides, free fatty acids, triglycerides, gastric juice, pancreatic enzymes, bile acids, and entero-endocrine hormones.

D. Nutrient Sources for the Ex Vivo Production of Microbiota

The growth of commensal microbiota is supported by a variety of nutrient sources. The nutrient sources contain but are not limited to hydrolyzed organic starch, hydrolyzed algal and yeast, peptone, dextrose, soluble starch, free fatty acid, and triglycerides, and other inorganic micro (vitamins and trace minerals) and macronutrients (sodium, potassium etc.). A modified half strength reinforced clostridial medium and modified MRS media can also be used for the commensal growth. L-cysteine can be used to control the gaseous oxygen and to keep the media in reduced state. Further, the biochemical contents of typical small and large intestine such as digestive enzymes, secondary and primary bile acids, and other bioactive compounds are also infused into the media to mimic human gut.

The organic nitrogen sources in the synthetic media include hydrolyzed fish extract and/or algae extract, and/or yeast extract. The synthetic media includes a protein source which is one or more of peptone and/or amino acids such as L-cysteine and the like. The carbohydrate sources in the synthetic media are dextrose and soluble starch. Further the synthetic media includes the metal salts preferably sodium chloride, potassium phosphate, ammonium citrate, magnesium sulfate, and manganese sulfate. The intestinal secretions present in the synthetic media are primary and secondary bile acids, enzymes, and mucus proteins. The synthetic media is maintained at a slightly neutral to acidic pH around 6.8.

The cartridge is infused with nutrients and metabolites normally present in intestine are hydrolyzed amino acids, inulin, oligofructosides, galactofructosides, free fatty acids, triglycerides, gastric juice, pancreatic enzymes, bile acids, and entero-endocrine hormones.

E. Composition of Seed Cultures

Further the cartridges are infused with seed culture, the seed culture primarily containing the microorganisms such as but not limited to, human-derived *Bacteriodetes, Prevotella, Xylanibacter, Facaelibacterium, Eubacterium, Subdoligranulum, Parabacteriodetes, Clostridium leptum, Clostridium coccoides, Ruminococcus, Collinsella, Roseburia, Akkermansia, Veillonella, Bifidobacterium, Verrucomicrobia, Lactobacillus, Escherichia* (from the Enterobacteriaceae family), *Desulfovibrio, Saccharomyces boulardiim, Cladosporium, Pentatrichomonas, Chilomastix, Entamoeba dispar,* gut microbiome viruses (e.g., phages) and the like.

F. Harvesting Cultured Microbiota

After culturing and achieving the required properties in the culture, the humanized commensal gut microbiota are harvested. After harvesting, the harvested humanized commensal gut microbiota are formulated as a freeze-dried (lyophilized) stable powder form in therapeutic delivery forms such as but not limited to capsules, sachets, rectal enema, rectal suppositories, creams, gels, oral solutions and the like. The harvested humanized commensal gut microbiota of can be administered via food and beverages such as but not limited to juices, milk, physiological saline, water, food and the like.

IV. Methods of Treatment

One embodiment provides a method for the treatment of metabolic disorders. The method includes obtaining a microbiota sample from healthy human donor and scrutinizing and purifying the same. Further the method includes, culturing the microbiota sample obtained from healthy human donor in a zig zag column system packed with cartridges that are designed to mimic the human gut lining, in a synthetic culture media supplemented with nutrients and metabolites normally present in intestine; harvesting and administering the microbiota to a patient in need of metabolic disorder treatment. Ex vivo produced human gut microbiota can be used to treat disorders including but not limited to, crohns disease (CD), inflammatory bowel disease (IBD), type 1 diabetes (T1D), type 2 diabetes (T2D) obesity, colitis, cancers, steatosis, atherosclerosis, Parkinson's disease, Alzheimer's disease, depressive disorders, malignancy, infectious diarrhea, necrotizing enterocolitis, and esophagitis.

Another embodiment provides a method for the production of a designed human gut microbiota expressing a functional bioactive molecule in gut of a patient undergoing a therapy. For example, the microbiota can genetically engineered to secrete a therapeutic protein, peptide, lipid, or small molecule. The method for production of designed microbiota includes obtaining a plurality of microbiota samples from healthy human donors. The human donors are inspected with respect to their health and credibility before taking the samples. Further, configuring a zig zag column system packed with cartridges designed to mimic the human gut lining, provides a metabolic situation for culturing the samples of gut microbiota. The method includes culturing the plurality of microbiota samples obtained from healthy human donors, in a synthetic culture media supplemented with nutrients and metabolites normally present in intestine, under physiological conditions to express functional bioactive molecules. Once the culture is ready, the culture is harvested and administered into the gastrointestinal tract of a patient in need thereof. The functional bioactive molecules produced in the ex vivo produced gut microbiota include, but are not limited to bone morphogenetic protein (BMP), e (EPO), g (G-CSF), g (GM-CSF), interferon alpha, interferon beta, interferon gamma, interleukin 2 (IL-2), interleukin 11 (IL-11), mammary-associated serum amyloid protein (M-SAA) and the like.

Human gut microbiota compositions described herein can be used to treat bone-related conditions, anemia, neutropenia, fungal infections, hepatitis C, multiple sclerosis, cancer, thrombocytopenia, chronic granulomatous disease, osteoporosis and the like.

In another embodiment, the preparation and assembly of the column includes the steps of: loading the cartridges into the columns; packing the column with secondary substrates; and assembling the loaded and packed columns in a zig-zag manner through connectors from their edges. In one of the preferred embodiment, a synthetic media, and nutrients and metabolites normally present in intestine are infused in the cartridge during culturing.

In another embodiment, the synthetic media includes: organic nitrogen sources, protein sources, carbohydrate sources, metal salts, intestinal secretions, enzymes, vitamins, and trace minerals maintained at a slightly neutral to acidic pH.

In another embodiment, the organic nitrogen source is one or more from hydrolyzed fish extract and/or algae extract, and/or yeast extract.

In another embodiment, the protein source is one or more from peptone and/or amino acids such as L-cysteine and the like.

In another embodiment, the carbohydrate sources are dextrose and soluble starch.

In another embodiment, the metal salts are sodium chloride, potassium phosphate, ammonium citrate, magnesium sulfate, and manganese sulfate. In one of the preferred embodiment, the intestinal secretions are primary and secondary bile acids, enzymes, and mucus proteins.

In another embodiment, the slightly neutral to acidic pH is around 6.8.

In another embodiment, the nutrients and metabolites normally present in intestine are hydrolyzed amino acids, inulin, oligofructosides, galactofructosides, free fatty acids, triglycerides, gastric juice, pancreatic enzymes, bile acids, and entero-endocrine hormones.

In another embodiment, the seed culture primarily includes the genus such as but not limited to, Human-derived *Bacteriodetes, Prevotella, Xylanibacter, Facaelibacterium, Eubacterium, Subdoligranulum, Parabacteriodetes, Clostridium leptum, Clostridium coccoides, Ruminococcus, Collinsella, Roseburia, Akkermansia, Veillonella, Bifidobacterium, Verrucomicrobia, Lactobacillus, Escherichia* (from the Enterobacteriaceae family), *Desulfovibrio, Saccharomyces boulardiim, Cladosporium, Pentatrichomonas, Chilomastix, Entamoeba dispar*, gut microbiome viruses (e.g. phages) and the like.

In another embodiment, the harvested humanized commensal gut microbiota are administered in optimally freeze-dried stable powder form via therapeutic delivery forms such as but not limited to capsules, sachets, rectal enema, rectal suppositories, creams, gels, oral solutions and the like.

In another embodiment, the harvested humanized commensal gut microbiota are administered in food and beverages such as but not limited to juices, milk, physiological saline, water, food and the like.

In one embodiment, a method for the treatment of metabolic disorders includes obtaining a microbiome/microbiota sample from healthy human donor; culturing the microbiome sample obtained from healthy human donor in a zig zag column system packed with cartridges that are designed to mimic the human gut lining, in a synthetic culture media supplemented with nutrients and metabolites normally present in intestine; harvesting and administering the microbiome to a patient in need of metabolic disorder treatment.

In one embodiment, the metabolic disorder is Crohns disease (CD), inflammatory bowel disease (IBD), type 1 diabetes (T1D), type 2 diabetes (T2D) obesity, colitis, cancers, steatosis, atherosclerosis, Parkinson's disease, Alzheimer's disease, depressive disorders, malignancy, infectious diarrhea, necrotizing enterocolitis, and esophagitis.

In one embodiment, a method for production of designed microbiota expressing a functional bioactive molecule in gut of a patient undergoing a therapy, includes: obtaining a plurality of microbiota samples from healthy human donors; configuring a zig zag column system packed with cartridges designed to mimic the human gut lining, to provide a metabolic situation; culturing the plurality of microbiome samples obtained from healthy human donors, in a synthetic culture media supplemented with nutrients and metabolites normally present in intestine, under the metabolic situation to adapt in expressing the functional bioactive molecules;

harvesting and administering the microbiota to the patient undergoing the therapy for expressing the functional bioactive molecule.

In one embodiment, the functional bioactive molecules are but not limited to Bone morphogenetic protein (BMP), Erythropoietin (EPO), Granulocyte colony-stimulating factor (G-CSF), Granulocyte macrophage colony-stimulating factor (GM-CSF), Interferon alpha, Interferon beta, Interferon gamma, Interleukin 2 (IL-2), Interleukin 11 (IL-11), Mammary-associated serum amyloid protein (M-SAA), Humanin (Alzheimer's Disease preventing peptide) and the like.

In one embodiment, the patient is undergoing treatment for an illness that includes but is not limited to bone-related conditions, anemia, neutropenia, fungal infections, hepatitis C, multiple sclerosis, cancer, thrombocytopenia, chronic granulomatous disease, osteoporosis and the like.

In one embodiment, the disclosed systems and methods can be used for production of designed microbiota expressing functional bioactive molecules in gut. The microbiota can be shaped into a functional organ to do critical bodily metabolic functions. In order to teach or adapt the commensal microbiota to particular a metabolic situation, a specific metabolic profile can be mimicked in the microniche and the commensal microbiota can be forced to evolve to better adapt to that profile by optimally switching into that metabolic genomic expression patterns. For example, for chemotherapy cancer patients, the commensal microbiota can be designed to perform key metabolic functions for the body. The organ systems might not be doing the intended optimal function because of the chemo-induced cellular damage. For example, functionally selected microbiota can temporarily make key cellular metabolites, which the patient needs until the patient's organs are revived fully. This can include growth-hormone stimulating peptides, neuroendocrine agents, endorphins, and key enzymes to complement vital functions for the body. Complex glycolysated protein metabolites such as cytokines (IL-2, haemopoietic growth factors, interferons, EGF) can be made by fungal microbiota (mycobiota). *Saccharomyces boulardii, Cladosporium, Pentatrichomonas, Chilomastix* and *Entamoeba dispar* are common eukaryotic commensal gut microbiota which can make complex glycolysated proteins.

Global analysis of bacterial communities demonstrates that host-associated communities are quite distinct from their free-living counterparts. The common patterns of diversity in the gut microbiome seen across the three domains of life are likely driven by the fact that host-associated environments, and especially the gut, are unique microbial habitats that are difficult to colonize because the stable, warm, low-oxygen, and eutrophic conditions represent an extreme environment. Eukaryotes that live in the gut are anaerobic or microaerophilic, and in most cases have highly reduced mitochondria. The collection of genes needed to make the specific molecules are induced into the functional microbiome in a forced evolution. The microbiome is highly adaptable functional genome which can be modulated by design.

A partial list of bioactive molecules that can be expressed by gut commensal flora include: bone morphogenetic protein (BMP), used to treat bone-related conditions; erythropoietin (EPO), used to treat anemia; granulocyte colony-stimulating factor (G-CSF), used to treat neutropenia in cancer patients; granulocyte macrophage colony-stimulating factor (GM-CSF), used to treat neutropenia and fungal infections in cancer patients; interferon alpha, used to treat hepatitis C and multiple sclerosis; interferon beta, used to treat multiple sclerosis; interleukin 2 (IL-2), used to treat cancer; interleukin 11 (IL-11), used to treat thrombocytopenia in cancer patients; interferon gamma is used to treat chronic granulomatous disease and osteoporosis; and mammary-associated serum amyloid protein (M-SAA).

In one embodiment, the disclosed systems and methods can be used to design high health promoting probiotics. The highly adhesive health promoting probiotic phenotypes can be evolved using this technology. For example, a health promoting probiotic, which has less colonizing capacity, can be adapted for better colonizing capacity. Health promoting probiotic consortium can also be humanized with the current technology. In this embodiment, a less adherent strain is co-incubated with core microbiota for 1 week and then harvested with the core-microbiota. The strain is forced to adapt to the human adhesive molecule via changes in the selective expression of its genes or by acquiring adhesive genes from the core-microbiome.

In another embodiment, the disclosed systems and methods can be used to study the specific effect of diet and dietary components on the gut microbiota. The disclosed devices can be used to study the effect of different diet components on the core commensal microbiota of humans. By adding different diet components into the substrate-device, several diet components can be simulated including the following: high fat diet, low fat diet, high sugar diet, low sugar diets, high protein diet, low protein diet, high fiber diet, low fiber diet, and a balanced diet.

Microbiomes from lean/obese human subjects can be used to see the dietary effect on the microbiome genomic and diversity signature overtime. Microbiota from a lean human can be used to mass culture in the device as a interventional formulation for metabolic disorders such as type II diabetes, obesity etc.

In another embodiment, the disclosed systems and methods can be used to design specific diet adapted designer gut commensal microbiota. The effect of the different diet regimes and how it affects the commensal flora can be studied. A better adapted core microbiota for each dietary regimes can be harvested and transplanted to human for better digestion and health benefits. The microbiota can be grown on plant-based diet, fruit-based diet, meat-based diet, milk-based diet, or a balanced diet regime (plant+meat+milk).

Hydrolyzed plant or meat protein or other nutrients can be infused into the device and changes in the core commensal flora and microbiome can be monitored to identify different aspects of growth and metabolism, and its effect on the patient.

In another embodiment, the disclosed systems and methods can be used to design a gut commensal microbiota with specific energy utilization ratio for metabolic disorders. Energy harvest and utilization of intake-food is an essential predictor of metabolic disorders. The device can be used to design an optimum group of bacteria which will metabolize the food in relative proportion which will obviate any metabolic disorders. For example, better enzyme producing groups and better short-chain fatty acid producing groups.

In another embodiment, the disclosed systems and methods can be used to study the effect of artificial sweetener on the commensal gut flora. Several studies have shown that artificial sweeteners (Aspartame, Cyclamate, Saccharin, Stevia, Sucralose) and its metabolites can have a negative impact on the symbiosis of commensal microbiome and overall gut digestive physiology. The effects of the artificial sweeteners on the core commensal microbiome can be studied by infusing these into the device and observing the changes.

In another embodiment, the disclosed systems and methods can be used to study the effect of alcohol on the commensal gut flora. Alcohol induced cirrhosis and non-alcoholic cirrhosis can be affected by the gut microbiome. A tailored synthetic humanized commensal microbiome can be made using the device for the management of cirrhosis. The gut microbiota affect the liver functions in several ways: 1) digesting the components and energy metabolism; 2) the production and synthesis of bile acid physiology; and 3) the diversification of the gut microbiome affected by alcohol. A designer commensal microbiota which can efficiently metabolize without changing the normal commensal microbiota can be designed using adaptive technology of core-microbiome and by mix-match of core commensal seed microbiota. A better alcohol metabolizing commensal flora can be designed.

Infusion of varying amounts of alcoholic beverages (consumer market, vodka, gin, beer, whisky) and observation of the changes in the quantitative and qualitative commensal flora over time can yield better understanding of the effects. The metabolic profiles can also be screened. The specific signature of alcohol and its effect on the metabolic can be studied including: 1) energy harvesting microbiome; 2) ethanol metabolizing; and 3) balanced ratio.

In another embodiment, the disclosed systems and methods can be used to study and optimize the metabolites from commensal microbiota and its physiological roles. Commensal microbiota makes several functional metabolites (peptides, hormones, proteins, lipoproteins, glycoproteins, small molecules) which promote several key metabolic and immune functions of the body. The device has specialized design to harvest the bacteria-free metabolites by an inner-chamber separated by 0.22 um membrane. A specialized attachment called functional screening port 110 is also integrated into the apparatus to do cell-screening studies on live cells. The functional screening portal 110 has a cell-growing surface with cell culture media and also has separate gas line for optimal oxygen+$CO_2$. The metabolites can be diffused into the screening portal 110 via a semi-permeable membrane which would not allow any bacteria to enter. This set-up can be used to real-time screening of specific activity of the metabolites on different cell types. Alternatively, the harvested substrate and core-commensal microbiome can be a source of metabolites (these can be put in PBS for overnight to release membrane proteins and secreted proteins and can be concentrated). The media used for the growing can also be periodically concentrated for secreted proteins and assayed for various functional studies. Non-limiting examples of different types of activity and screening include: protein fractions which have proliferation of specific T-cells (Th-17 cells) can be assay in T-cell proliferation assays; protein fractions which have T-cell selection can be studied in T-cell selection assays; bioactives with enterocyte differentiation can be assayed in cell-culture studies; bioactives with neuro-endocrine functions can be assayed in cell-culture studies; bioactives with natural killer cells proliferation assays can be determined in cell-culture studies; bioactives with commensal quorum sensing molecules can be studied with quorum sensing reporting assays; bioactives with antibacterial and antibiofilm can be assayed using specific pathogens and antibacterial and antibiofilm assays; bioactives with anti-inflammatory can be assayed using cell culture and cytokine assays; bioactives with pro-inflammatory can be assayed using cell culture and cytokine assays; bioactives with barrier and tight junction function and be assayed using 3-D organ models or animal models; bioactives with protein hydrolyzing (enzymes) can be assayed using protein-agar plates; and bioactives with specific enzyme activities can be studied using enzyme kinetic studies using substrates.

In another embodiment the disclosed systems and methods can be used to study the effect of changing the binding molecule of substrate matrix and its effect on commensal microbiota population. The substrate can be coated with different microbial adherence molecules. The gut bacteria adhere on the gut with different mechanisms. The main adherence proteins are fibronectin binding proteins, fibrinogen-binding proteins, collagen-binding proteins and other tight-junction binding proteins. The bacteria also bind with their pili and flagella to the cells. The mucin proteins can also have different binding molecules to bind commensal bacteria. The binding molecules are important colonizing host factors and are important parameters in defining commensal microbiome structure and evolution. The core inner highly bound microbiome serves as the source from which new populations are derived. Any long-term effect on the commensal stem cells or core-microbiome can have profound effect on the health of the human. Microbial surface component recognizing adhesive matrix molecules (MSCRAIVIM) are adhesive proteins that mediates initial attachment of bacteria to the host tissue. The adhesion can be mediated by degree hydrophobicity, neutral and hydrophilic or ionic interaction of the attachment between host and bacteria. Several classes of these molecules can be immobilized into the substrates cartridges and studied. The best mix of adherence molecules is used for harvesting the most—adapted substrates.

In another embodiment, the disclosed systems and methods can be used to study and design synthetic antimicrobial microbiota. An Eco biological Approach Rational design of microbial communities as biologic products can treat, prevent, cure, or mitigate infectious diseases or their squeal. Current approaches harness existing functional constituents of the microbiota and their products to restore health to the host. Physicians and clinician scientists use fecal microbiota transplants to treat infectious diseases such as *C. difficile* associated diarrhea, and researchers are developing the use of microbial bio therapeutics as adjunct therapy to antibiotic treatment for bacterial vaginosis. Commensal microbiota and microbiome with antimicrobial activity towards several bacteria can be designed by mixing and matching microbiota from several different human subjects. This is highly relevant towards enteric pathogens such as *Salmonella, Shigella, Enterotoxigenic E.coli,* and *Enterpathogenic E.coli* (EPEC), *Vibrio cholera*. Specific signature commensal flora which have adapted for a variety of physiological activities; antibacterial production, specific enzyme activity, reduced adherence, anti-aggregate formation, anti-quorum sensing activity, competitive exclusion and other signaling to reduce the load of pathogen can be designed into a single microbiome or group of microbiota.

One method to develop this signature core-commensal includes establishing different core-microbiota from different seed cultures including pathogens (for example, 8 log EPEC are added to the different cultures). The growth physiology of the EPEC on various core-microbiome is assessed. Growth reduction or growth promotional effects of core-microbiota are assayed. If a core-microbiota causes a 2-4 log reduction, it is subjected to further mix-match with other core-microbiomes.

In another embodiment, the disclosed systems and methods can be used for optimizing bacteriophage-treatment to reduce the antimicrobial resistance genes in the microbiome. Commensal flora is a constant source of antibiotic resistant genes (AMR). Bacteriophage can be used to reduce the load specific populations of microbes which harbor antimicrobial resistance genes. CRISP-Cas 9 gene cassettes can be used in specific phages to target populations of antimicrobial resistance flora and lyse those cells. After several rounds of phage-treatment, a specific microbiome can AMR gene-free. The commensal flora which is AMR-gene-free can then be used for several indications.

In another embodiment, the disclosed systems and methods can be used to study and design humanized commensal microbiota adapted bacteriophages for phage-therapy. Bacteriophages are an important element in the human gut microbiota. The ratio of different phages determines the relative ratio of different microbes in the gut. The device can be used for harvesting humanized commensal microbiota adapted bacteriophages which can maintain the gut commensal flora in a specific relative proportions.

In another embodiment, the disclosed systems and methods can be used to study relative metabolic functionality proportion of the commensal microflora. The microbiome of the commensal defines key metabolic functions which have important implications in digestion, energy homeostasis, neural and immune functions. The proportion of butyrate producers, short chain fatty acid producers, secondary bile acid metabolizers, mucin producers, mucin degraders and neuro-active peptide producers etc. are important in defining the effect of the commensal microbiota on the host health and metabolism.

A typical designer flora includes the relative percentage proportions of various metabolic groups, and can be as follows: butyrate producers—20-25%; short chain fatty acid producers—15-20%; mucin degrading organisms—10-12%; mucin producers—1-5%; digestive enzyme producers—10-15%; neuro-endocrine peptide producers—0.5-1.0%; secondary bile acid metabolizers (ursodeoxycholic acid and lithocholic acid)—2-5%; polyphenol and isothiocyanate producers—1-2%; tight junction protein production inducers—1-5%; and epigenetic modulators (histone deacetylase producers, DNA methylase producers etc.)—0.5-4%.

In another embodiment, the discloses systems and methods can be used for optimizing different methods for delivering the commensal microbiota for the treatment of a specific indication. The harvested commensal flora are intended to be use in several forms. The flora can be optimally freeze-dried into a stable powder form and used in the following forms of therapeutic delivery forms: capsules; sachets; rectal enema; rectal suppositories; creams or gels; sachet in powder form; and oral solution.

Further, specific doses can also be delivered via food and beverages including: juices; milk; physiological saline; water; and food.

In one embodiment, a typical formulation and dosage is: (a) A 250 mg commensal microbiota from a sachet suspended in an 8 oz juice twice daily for 2 weeks; (b) 1 g commensal microbiota formulated with a thickener as a rectal suppository; and (c) 500 mg gelatin capsule for oral delivery.

The disclosed systems and methods can be used to treat diabetes type II. Gut microbiota specific metabolites influence the signaling of various pathways which influences the glucose metabolism and insulin sensitivity in the human body. The optimum expression of incretins (glucose-dependent insulinotropic peptide (GIP) and glucagon-like peptide-1 (GLP-1), xenin, leptin, diacetlyghrelin and ghrelin are all vital components in glucose metabolism. Further, bile acid metabolism is also important pathway which have direct relevance on the glucose metabolism. Gut microbiota clearly influences all these elements. The disclosed systems and methods can be used to create humanized gut microbiota ex vivo by optimized production of all these metabolites in specific pre-determined level so as to use as a prophylactic control of pre-diabetic patients. These designer microbiota also increase the intestinal barrier so as to reduce the systemic endotoxemia which is another chronic cause of type II diabetes.

In another embodiment, the disclosed systems and methods can be used for the production of humanized designer phages that are adapted to the human gut microbiome. By co-culturing phages and various microbiota in the discloses system, real-time dynamics of microbial symbiosis in the human gut can be studied. Further how phage specifically shape microbiota and microbiome diversity can also be elucidated. Specific phages such as engineer bacteriophage that produces an antimicrobial compound that helps avoid bacteria such as enteroaggregative *Escherichia coli* or *Klebsiella* that are developing resistance to the phage, thereby increasing their value for treating associated childhood diseases. These humanized specific phage populations could be valuable for treating intestinal diseases that cause severe morbidity and mortality in developing countries as they can selectively destroy pathogenic bacteria. However, some bacteria rapidly develop resistance to the phage, which renders them useless. By inducing phage-infected bacteria to also release a toxic substance (bacteriocin), this would destroy any potentially resistant neighboring bacteria.

Food pathogens are a leading cause of death in children under five years old in the developing world but there are no effective vaccines due in part to the many different forms of the bacterium. The effects of the specific phages on the human gut microbes and its dynamics are evaluated both by sequencing to determine the quantities and types of bacteria in the gut, and by analyzing protein production in the bacteria and the mice, which will also reveal insight into the host immune response. The disclosed systems and methods can be used to develop a bacteriophage to destroy the diarrhea-causing bacterium *Shigella* or *Salmonella* or *Listeria monocytogenes*, and study its effect on microbial populations in the gut. How a unique phage-based editing of the gut microbiome and its functionality can be mimicked in the disclosed systems and methods. The disclosed systems and methods can be used for creating designer humanized phage-edited gut microbiota for various applications.

In another embodiment, the disclosed systems and methods can be used for studying the effects of various xenobiotics and their effect on the human microbiome/microbiota and thereby to the human body. Specific xenobiotic situations can be re-created in the disclosed system by infusing various drugs and the changes in the metabolomic, proteomic, metatranscriptomics, and metagenomic studies on the gut microbiome can be specifically elucidated.

The gut microbiota is a significant component of first-pass metabolism. Prior to entering systemic circulation and reaching the target tissue, orally ingested compounds are subject to metabolism in the intestine and liver, which decreases the eventual systemic drug concentration. The gut microbiota may metabolize compounds prior to absorption, after efflux from the intestinal epithelium or following biliary excretion from the liver.

Mechanisms that link the gut microbiota and xenobiotic metabolism include: gut microbiota can directly metabolize xenobiotics into active, inactive or toxic metabolites; xenobiotics may also shape the composition of the gut microbiota through antimicrobial activity or selective growth; gut microbiota can indirectly influence xenobiotics through the modulation of host pathways that are responsible for metabolism and transport; and this can be mediated by microbial metabolites or through the microbial modification of host metabolites.

Xenobiotics include antibiotics, therapeutics drugs, diet-derived bioactive molecules, and pollutants. In the following section, we will focus on the effects of the most described xenobiotics: antibiotics and host-targeted therapeutic drugs.

In another embodiment, the disclosed systems and methods can be used for creating a humanized microbiome/microbiota for increased human longevity. The study of the extreme limits of human lifespan may allow a better understanding of how human beings can escape, delay, or survive the most frequent age-related causes of morbidity, a peculiarity shown by long-living individuals. Longevity is a complex trait in which genetics, environment, and stochasticity concur to determine the chance to reach 100 or more years of age. Because of its impact on human metabolism and immunology, the gut microbiota has been proposed as a possible determinant of healthy aging. Indeed, the preservation of host-microbes homeostasis can counteract inflammation, intestinal permeability, and decline in bone and cognitive health. Aiming at deepening our knowledge on the relationship between the gut microbiota and a long-living host, we provide for the first time the phylogenetic microbiota analysis of semi-supercentenarians, i.e., 105-109 years old, in comparison to adults, elderly, and centenarians, thus reconstructing the longest available human microbiota trajectory along aging. the presence of a coremicrobiota of highly occurring, symbiotic bacterial taxa was highlighted (mostly belonging to the dominant Ruminococcaceae, Lachnospiraceae, and Bacteroidaceae families), with a cumulative abundance decreasing along with age. Aging is characterized by an increasing abundance of subdominant species, as well as a rearrangement in their co-occurrence network. These features are maintained in longevity and extreme longevity, but peculiarities emerged, especially in semi-supercentenarians, describing changes that, even accommodating opportunistic and allochthonous bacteria, might possibly support health maintenance during aging, such as an enrichment and/or higher prevalence of health-associated groups (e.g., *Akkermansia, Bifidobacterium*, and Christensenellaceae). Probiotics have been shown to be effective in restoring the microbiota changes of older subjects, promoting different aspects of health in elderly people as improving immune function and reducing inflammation. Whether modulation of GI microbiota composition, with multi-targeted interventions, could have an effect on the prevention of frailty remains to be further investigated in the perspective of improving the health status of frail 'high risk' older individuals. Further, recent studies have shown that gut microbial metabolites from pomegranate, berries, and nut produces Urolithin A, a mitophagy preventing natural compound. Urolithin A increases life expectancy by increasing the mitochondria levels in cells. In another embodiment the disclosed systems and methods can be used for creating a humanized microbiome/microbiota for high level of Urolithin A in human body.

In another embodiment, the disclosed systems and methods can be used isolate active gut microbiota from total gut microbiota. One of the most intriguing issues relates to understanding which microbial groups are active players in the maintenance of the microbiota homeostasis. Gut bacterial families were observed to appear or disappear on applying a cell sorting method in which flow cytometry was used to evaluate the active cells by pyronin-Y staining of RNA. This method was able to detect active bacteria, indicating that the active players differed from that observed in raw fecal material. Generally, observations showed that in the active fractions, the number of reads related to Bacteroidetes decreased whereas several families from Clostridiales (Firmicutes) were more highly represented. The active microbial cells can be differentiated from total flora by means of a tagging-technique based on the presence of RNA using pyronin-Y, a fluorescent stain for total RNA. Flow-cytometry cell sorting can be used to isolate active microbial fraction from fecal samples of healthy volunteers. The disclosed systems and methods can be used enrich and isolate bioactive and health promoting gut microbiota (e.g. clostridales) from total gut microbiota.

In another embodiment, the disclosed systems and methods can be used produce gut microbiota producing excess amounts of trehalose. Recent studies have shown that trehalose-a disaccharide molecule- is highly neuroprotective and might have significant benefits in various neural diseases. The trehalose biosynthetic genes, otsBA operon, can be used for creating a signature trehalose expressing microbiome repertoire using the disclosed systems and methods. This humanized signature microbiota can be used for treatment of neural disorders.

The various elements and/or embodiments of the invention for production of humanized commensal gut microbiome as described in the present disclosure may be related in the following exemplary fashion. It is not intended to limit the scope or nature of the relationships between the various elements and objectives and the following examples are presented as illustrative examples only.

EXAMPLES

Example 1

Production of Humanized Commensal Gut Microbiome for Various Treatments

Method

Microbiota from healthy human volunteers is collected by endoscopy (rectal or oral) and from fecal samples. Other methods such as samples left after surgical procedures can also be used to procure healthy microbiota and would be apparent for any person skilled in the art.

If the sample is a fecal sample, the donors are screened for the presence of ova and parasites in the stool culture. Specific pathogens to be screened for include, but are not limited to the following: *Salmonella, Shigella, Escherichia coli,* O157:H7, *Yersinia enterocolitica; Campylobacter; Clostridium difficile* toxins A and B; *Cryptosporidium* antigen and *Giardia* antigen.

If the sample is a serum sample, the sample is screened for pathogens includes but not limited to the following: HIV-1 and HIV-2; Hepatitis A, B, and C; rapid plasma regain; fluorescent treponemal antibody; and absorbed *Treponema pallidum*.

This step is necessary in order to ascertain that the commensal microbiota should be devoid of disease causing Blastocystis (IBD) and *Candida* (leaky gut), *Entamoeba histolytica, Cryptosporidium parvum, Pneumocystis carnii,*

*microsporidia, Giardia intestinalis, Encephalitozoon, Toxoplasma, Naegleria* and the like.

Donors are excluded, if they matched any alarming condition such as but not limited to, BMI>30, active smoking, known chronic diseases, antibiotic usage in the past 6 months and detection of inflammation and/or infection in blood- and/or fecal assessments. Donor blood is also assessed for full blood count and serological testing for hepatitis A, B and C; HIV-1 and 2 and *Treponema pallidum*. Donor stools are specifically screened for enteropathogens. Bacterial culture is performed to detect the following enteropathogens: *Salmonella* spp, *Shigella* spp, *Yersinia enterocolitica* and *Y. pseudotuberculosis, Campylobacter* spp, and *Aeromonas* spp. Microscopic examination is performed in search for eggs, cysts and/or larvae of parasites and membrane ELISA is done to detect *C. difficile* toxins A and B, and glutamate dehydrogenase. For the latter, PCR is performed in case of discordance between results of toxins and glutamate. Patients undergo full ileocolonoscopy with calculation of the Crohn's disease Endoscopic Index of Severity (CDEIS) and Simplified Endoscopic Activity score (SES-CD) and Mayo endoscopy sub score (for UC) at baseline and week 8 after FMT. C-reactive protein (CRP) and clinical disease activity were collected using the Crohn's disease Activity Index (CDAI) for CD and the Mayo score for UC. Patients are followed-up for at least 6 months.

The clinician who undertakes the procedure estimates the risk that the donor had recently contracted a transmissible disease, such as HIV or hepatitis, as well as rule out potential exposure to pathogenic agents that are not identified by laboratory methods to a high degree of sensitivity. This can be facilitated by eliminating donors with a history of engaging in high-risk behaviors, such as illicit drug use, sexual encounters with multiple partners, or unprotected sexual activity. Additional potential exclusions include donors with a history of incarceration, tattoo or body piercing in the past 6 months, current or known exposure to a communicable disease, use of immunosuppressant agents, or antibiotics within the last 3 months. Travel within the past 6 months to an area known to be a risk factor for diarrheal illness or other infectious diseases should also be considered in the analysis of donors. It is ideal to have donors with no known genetic, infectious and metabolic diseases and any known family history of cancers. The donors with minimum use of antibiotics and a good life style (exercise, active life style, good diet habits, non-smoking and non-alcoholics) are preferred. The microbiota samples are purified, catalogued and stored in −80° C. until further used. The microbiome is sequenced to identify the relative proportions and diversity of microbiota. After evaluation of the donor characteristics, genomic and species diversity of the catalogued microbiomes, several seed microbiota (SM) are prepared. Seed microbiota can come from a single donor or from multiple donors. The approximate composition of major genus in the seed culture is as follows: human-derived *Bacteriodetes; Prevotella; Xylanibacter; Facaelibacterium; Eubacterium; Subdoligranulum; Parabacteriodetes; Clostridium leptum; Clostridium coccoides; Ruminococcus; Collinsella; Roseburia; Akkermansia; Veillonella; Bifidobacterium; Verrucomicrobia; Lactobacillus; Escherichia* (from the Enterobacteriaceae family); *Desulfovibrio; Saccharomyces boulardii; Cladosporium, Pentatrichomonas, Chilomastix; Entamoeba dispar* and various gut viruses (e.g., phages)

Preparation

The cartridges are processed to immobilize human cells such as gastrointestinal cells, adhesive proteins, and mucus proteins. The cartridges are loaded into the column and assembled. The secondary substrates such as glass wool or perforated sponge are tightly packed into the column. The prepared synthetic media also contains bile acids and enzymes and other hydrolyzed nutrients in proportion, which are similar to human gut. The seed microbiota is mixed in the prepared media and infused into the cartridge column. After initial growth of the seed culture, the culture system infused with nutrients and metabolites normally present in intestine to mimic the human intestine physiology.

The media composition used for culturing the microbiota is prepared to 1 liter having the following composition and maintained to a pH of 6.8: hydrolyzed fish extract or algae extract: 2.5 g; peptone: 2.5 g; sodium chloride: 1.25 g; dextrose: 1.25 g; yeast extract: 0.5 g; soluble starch: 0.3 g; l-cysteine: 0.35 g; potassium phosphate: 0.25 g; ammonium citrate: 0.25 g; magnesium sulfate: 0.05 g; manganese sulfate: 0.02 g; bile acid mix (primary and secondary bile acids): 0.3 ml; enzyme mix, digestive enzymes: 0.3; mucus proteins: 0.1 ml; trace mineral and vitamin solution: 1 ml; carbohydrate—10-60 g; resistant starch–40 g; hydrolyzed amino acids—10 g; inulin, oligofructosides, and galactofructosides; free fatty acids and triglycerides; gastric juice and various enzymes; pancreatic enzymes; bile acids; and entero-endocrine hormones.

The culture system is also infused with nutrients and metabolites normally present in the intestine and several bioactive media components are added depending on the specific adaptive need of the commensal flora.

Culturing

The excess liquid media from the column is drained off and the gaseous system is activated to create and maintain a gradient of aerobic to micro-aerophilic to anaerobic atmosphere inside the column and cartridges. High humidity (70-80%) is maintained inside the column and chamber to avoid drying of the substrate. A small quantity of fresh media (100 ml) is allowed to diffuse through the column to give fresh nutrients every 6-8 hr. The seed culture is allowed to grow for 24-48 hrs. The core commensal microbiota are established in 48-72 hrs and has the signature adherence expression profile and phenotype of human gut commensals.

Harvesting

The cartridges are taken out from the column and immersed in physiological saline or PBS. If necessary, processing is conducted under an anaerobic chamber to safeguard the viability of anaerobic flora. The commensal flora can be detached from the substrate by gently vortexing, sonication or mechanical stirring. The harvested microbes are spun down and stored under −80° C. with appropriate cryoprotectants until used.

Determining the Microbiome and Diversity of the flora

The quantitative and qualitative counts are estimated for the flora via different analytical methods. The diversity, resistance gene profile and percentage representative flora is determined via genomic and sequencing methods. The material after quality control is again gave a batch and lot number and ready to use.

Example 2

Study of Species Diversity, Relative Proportion and Resistance Gene Profiling of the Commensal Flora Humanized commensal microbiota with high diversity and proportion are produced from a seed culture, and can deliver metabolic benefits when administered to a host. The resistance genes of the microbiome are profiled for the presence of any resistance genes. Increased concentration of clostridial cluster XI and XVI is a feature of designer commensal flora. A typical designer commensal flora includes 500-1000 different species with below relative percentage proportions:
*Bacteriodetes:* 22-25%
*Prevotella:* 10 %
*Faecalibacterium:* 5-8%
*Eubacterium:* 3-5%
*Subdoligranulum:* 0.5-1.0%
*Roseburia:* 0.25-0.5%
Further, the following typical pathogens presences are screened for exclusion:
*Helicobacter pyroli*
*Acidovorax*
*Enterococcus faecalis*
Genotoxic *E coli*
Genotoxic *B. fragalis*
*Fusobacterium nucleatum*
*S. bovis*
*Salmonella*
*C. difficile*

The human gut microbiota is dominated by five bacterial phyla (Firmicutes, Bacteroidetes, Actinobacteria, Proteobacteria and Verrucomicrobia) and one Archaea (Euryarchaeota). The less prevalent bacterial groups are distributed among Cyanobacteria, Fusobacteria, Lentisphaerae, Spirochaetes and TM7. The Firmicutes phylum contains relevant genera, including *Ruminococcus, Clostridium, Lactobacillus* (several strains of which are probiotics), and the butyrate producers Eubacterium, Faecalibacterium and Roseburia. In Bacteroidetes, *Bacteroides, Prevotella* and *Xylanibacter* degrade a variety of complex glycans. The Actinobacteria phylum includes *Collinsella* and *Bifidobacterium* (which contains probiotic strains). Common Proteobacteria are *Escherichia* (from the Enterobacteriaceae family) and *Desulfovibrio* (which contains sulphate-reducing bacteria). Verrucomicrobia was recently discovered and includes *Akkermansia* (which are specialized for mucus degradation). Euryarchaeota contains the prevalent Methanobrevibacter (which is involved in the continuation of intestinal methanogenesis). Complex carbohydrates such as dietary fiber, are metabolized by the colonic microbiota to oligosaccharides and monosaccharides and then fermented to short-chain fatty acid end-products, mainly acetate, propionate and butyrate. Short-chain fatty acids are absorbed in the colon, where butyrate provides energy for colonic epithelial cells, and acetate and propionate reach the liver and peripheral organs, where they are substrates for gluconeogenesis and lipogenesis. In addition to being energy sources, short-chain fatty acids control colonic gene expression by inhibiting the enzyme histone deacetylase (HDAC) and metabolic regulation by signaling through G-protein-coupled receptors (GPCRs), such as GPR41 or GPR43. Gut commensal bacteria live in normobiosis with the host and have important metabolic, protective, and trophic functions. The overall composition of the gut microbiota and the presence or absence of specific species is important for homeostasis and tolerance of the immune system. The development of high-throughput sequencing technologies has facilitated metagenomics research in determining the complexity and immense diversity of microbial life in various ecological niches. Metagenomic analysis demonstrated significant interindividual variation in gut microbiota composition, described as continuous gradients or distinct microbiota clusters ("enterotypes" or "co-abundance groups"). At present, there is no clear evidence for a single pathogen causing IBD. On the other hand, marked alterations in microbial communities are observed in IBD patients. Patients with IBD have fewer anti-inflammatory bacteria and/or more pro-inflammatory bacteria. Such dysbiosis is well described in CD and more recently also in UC. A reduction of *F. prausnitzii* is the most replicated species-specific finding so far and is confirmed in fecal and mucosal samples. This species has anti-inflammatory and immunomodulary effects in vivo and in vitro. In addition to *F. prausnitzii*, the adherent invasive *Escherichia coli* (AIEC) is increased in ileal mucosa of CD patients and may sustain inflammation.

Example 3

Treatment for Ulcerative Colitis (UC) and Crohns Disease (CD) using Commensal Microbiome Therapy The commensal microbiota therapy for Crohns Disease and Ulcerative Colitis includes a highly diversified humanized commensal flora prepared from multiple donors and screened for species diversity and exclusion UC/CD-specific flora. The commensal flora is screened for resistome and other screening criteria as described in Example-1. The lyophilized commensal microbiota is delivered in two formats for the patients. Retention enema (500 mg commensal microbiome in 50 ml PBS) and as a capsule (500 mg capsule, one capsule/day). Patients were scheduled for a flexible sigmoidoscopy and also completed baseline questionnaires to obtain demographic information, Mayo score, and Inflammatory Bowel Disease questionnaire score.

Participants were given 50 mL commensal microbiome in PBS as a retention enema once per week for 8 weeks. The enema was administered with the patient in the left lateral position with instructions to retain this for at least 20 minutes. Patients provided stool samples each week before receiving their retention enema and samples were stored at −20° C. for fecal microbiota analysis. The primary outcome was UC/CD remission at week 7, defined as a full Mayo score <3 and complete healing of the mucosa at flexible sigmoidoscopy (endoscopic Mayo score 1/40). Secondary outcomes included improvement in UC symptoms, as well as change in Mayo, Inflammatory Bowel Disease Questionnaire, and EQ-5D scores. Fecal transplant was used as the comparative treatment for comparison.

There were 25 patients on each treatment paradigm and the clinical outcomes for efficacy has been provided in the table below:

| Outcome | Fecal Transplantation (n-24) | Commensal Microbiome (n-26) |
| --- | --- | --- |
| Clinical remission, (%) | 08 | 62 |
| Clinical response (%) | 24 | 68 |
| Full Mayo score | 6.9 | 1.2 |
| Proportion with high ESR, (%) | 45 | 22 |
| Proportion with high CRP, (%) | 56 | 18 |
| Patients with serious adverse events (%) | 16 | 02 |
| Diversified Microbiome transplant efficiency (%) | 18 | 74 |

An important factor for determining the success of fecal transplant and commensal microbiota therapy is restoration of microbial diversity after treatment. Additionally, changes in microbial community structure, such as restoration of key Firmicutes and Bacteroidetes species with a decrease in Proteobacteria, appear to be required to outcompete *C. difficile*. A decrease in Lachnospiraceae has been associated with severe CDI, suggesting a protective role for members of this family, and administration of a cocktail containing a member of Lachnospiraceae was reported to cure CDI in mice. Furthermore, successful FMT restores members of Lachnospiraceae and other butyrate-producing organisms, supporting their potential role in outcompeting *C. difficile*. A more recent study that treatment with either a consortium of bacteria or *Clostridium scindens*, both of which harbor the gene encoding 7-hydroxysteroid dehydrogenase required for secondary bile acid synthesis can ameliorate CDI in mice. Overall, the commensal microbiota therapy outperformed fecal transplant in all the clinical outcomes suggesting the use of commensal microbiota technology as an effective intervention of UC and CD.

Example 4

Treatment of Infectious Diarrhea and Necrotizing Enterocolitis by Expression of Mammary-associated Serum Amyloid Protein (M-SAA3).

Two seed microbiomes (X1 and Y1) were cultured and evolved in the commensal microbiota device. The genes for the 42-mer Mammary-associated serum amyloid protein (M-SAA3) Sequence: COOH-QGWLTFLKAAGQGTKD-MWKAYSD MKEANYKKFRQILPCLGEL-NH2 (SEQ ID NO:1) were synthesized. (M-SAA3), an acute phase protein, is a component of milk but is present at particularly high concentrations in colostrum. Previous studies have shown that a 10-mer peptide derived from the N-terminal region of the 42-mer human M-SAA3 may have a role as an anti-infective, as it prevents enteropathogenic *Escherichia coli* (EPEC) adherence in vitro, both to human intestinal epithelial cells and small intestinal mucosa. This antiadhesive effect is mediated by enhancement of innate protection through stimulation of production of the intestinal mucin MUC3, a mechanism also demonstrated for the probiotic Lactobacillus GG. The 10-mer peptide, consisting of residues two to 11 of the N-terminal region of the human 42-mer protein contains a TFLK motif. The gene can be transferred to the microbiome by several methods:

1) Passive transfer: The synthetic gene in high concentration (2-3 mg DNA) is infused into the mature evolved microbiome in the apparatus of the invention with the media and allowed to grow aerobically for 2-3 days. As there are inherent microbial physiology to uptake gene fragments in the complex biofilm consortium of the microbiome, the microbiome XY takes up the gene into the gene repertoire by passive methods. The M-SAA3 gene is transferred to gut commensal microbiome by this method.

2) Conjugative transfer: The gene is cloned into a plasmid in a conjugative transfer strain of *E.coli*-S17-1 (with conjugative plasmids: pARO181 or pARO190). This strain is infused into the mature evolved microbiome in the apparatus with the media and allowed to grow aerobically for 2-3 days. The M-SAA3 gene is transferred to gut commensal flora by this method. The aerobic *E.coli*-S17-1 were cured of the culture system by repeated washing and anaerobic culturing.

3) Active transfer by protoplast: The microbiota are harvested and put in an isotonic solution. At least partial protoplasting of the microbiome is carried out following a modification of a method previously described. Briefly, cells are grown in 20 ml of Penassay broth (PAB) at 37° C. under anaerobic conditions until the onset of the stationary phase of growth (OD600=1.7-2). Subsequently, cells are collected by centrifugation, suspended in 10 ml of SMPP medium (0.3% bovine serum albumin, 5% 2 M sucrose, 25% 4× PAB, 50% 2× SMM), composition of 2×SMM being 1 M sucrose, 0.04 M maleic acid and 0.04 MgCl2 (pH 6.5), and protoplasts are obtained after incubation at 37° C. on a rotary shaker at 100 rpm for 30 min in presence of lysozyme (10 mg/ml) and mutanolysin (75 U/ml). The presence of protoplasts is verified by phase contrast microscopy. Protoplasts are then carefully harvested by centrifugation at 5200×g and 4 ° C. for 5 min, washed twice with ice cold washing buffer (SMMP medium without PAB), and finally suspended in this solution. For each transformation, a 2 ml protoplast preparation is mixed with 15 µg of plasmid DNA or synthetic gene (DNA) in a 15 ml tube. 1.5 ml of 40% polyethylene glycol is immediately added and incubated for 2 minutes at room temperature. Protoplasts are diluted with 5 ml SMMP and harvested by gentle centrifugation and removal of supernatant. After addition of 500 µl SMMP cells are incubated overnight at 37 ° C. with gentle shaking. Then cells are added to apparatus and incubated for 2-3 days at 37 ° C. Confirmation of the gene transfer is confirmed by sequencing the microbiome.

4) Gene-transfer in commensal microbiota device: The mature microbiota in the apparatus is added with 2 M sucrose solution and then subjected with partial removal of cell wall by incubating with lysozyme and mutanolysin for 8 hrs at 37° C. 25-50 µg of plasmid DNA or synthetic gene (DNA) is infused after and allowed to grow for 2-3 days. Several strains of the commensal flora take up the DNA. A cell wall-recovery media is then infused into the device. Confirmation of the gene transfer was confirmed by sequencing the microbiome.

The microbiota $XY^{M-SAA3+}$ are harvested and lyophilized. The lyophilized $XY^{M-SAA3+}$ is made into 500 mg gelatin capsules (for adult patients) or oral PBS solution with 500 mg lyophilized powder. Patients with bloody diarrhea or necrotizing enterocolitis are treated with 2 capsules daily for 7 days or oral gavage of the solution once daily for 7 days.

The major mechanisms of action of $XY^{M-SAA3+}$ are:

1) Increased intestinal MUC2 and MUC3 expression (5-10 fold) by the stimulation of M-SAA3 and mucin adapted commensal strains in the $XY^{M-SAA3+}$;

2) Increased intestinal Claudin3 expression (20-25 fold) by the stimulation highly adapted commensal strains in the $XY^{M-SAA3+}$ thereby rendering enhanced gut barrier function;

3) Deceased intestinal adherence enteropathogenic *Escherichia coli* (EPEC) or enterotoxigenic *Escherichia coli* (ETEC) or enteroinvasive *Escherichia coli* (EIEC) because of expression of M-SAA3 and highly adapted commensal strains in the $XYM^{-SAA3+}$; and 4) Increased microbiome diversity and increased presence of mucin degraders in the highly adapted commensal strains in the $XY^{M-SAA3-}$.

Example 5

To Study the Antibiotic Resistance Evolution in the Commensal Flora

The commensal microbiota device can be used to study or model how antimicrobial resistance (AMR) evolves in commensal flora. The commensal flora is a reservoir of AMR genes or resistome. The mechanism of AMR evolution of commensal flora is still unknown. Even without antibiotics, the commensal flora can develop and exhibit resistance phenotypes towards multiple antibiotics. Some of the resistance genes are hidden in the commensal microbiome while others are expressed phenotypically in the GI tract.

a) How to study the evolution of resistance genes without antibiotic treatment:

The commensal microbiota (flora X) under study are profiled for total resistance gene and diversity on a designed time (Time 0, X0)

The flora X is cultured in the microbiota apparatus without any antibiotic selective pressure for 4-15 days as described previously (Example-1). After specific time-intervals the resistome of the flora X can be profiled to real-time changes with respect to the evolution of AMR. Also the phenotypic expression of AMR towards multiple antibiotics can be studied. Information on key groups of bacteria and genes which are susceptible for AMR generation can be identified. Specific phenotypes which are more prone to AMR can be identified (biofilm phenotype, aggregates, adhesive communities, specific consortiums of commensals). The prominent mutations can be used for predictive analytics for AMR resistance b) How to study the evolution of resistance genes with antibiotic treatment:

The same method of AMR studies can be studied with antibiotic selection pressure using single antibiotics or multiple antibiotic. A single antibiotic or multiple antibiotics are mixed with the media and at periodical intervals samples are taken to analyze for species diversity, resistome profiling, identifying AMR vulnerable genus and species, mutations and phenotypic expression etc., and the results have been discussed in the table below:

| Without Antibiotic | With Antibiotics |
|---|---|
| Non-adaptive mutation | Adaptive mutations |
| Spontaneous mutation | Directed mutations under selective pressure |
| Phenotypic variation, biofilm, nutrients drive AMR | Selection is the major force for mutation |
| Slower rate of AMR | Phenotypic variation, selection of AMR groups in a commensal community |
| Non-specific towards antibiotics | Specific mutations/AMR towards antibiotics or classes of antibiotics |
| Does not change the normal dynamics of commensal flora (quantitative and qualitative change) | Change the dynamics of commensal (quantitative and qualitative change) |

Example 6

Treatment of Anti-Hemorrhoidal Agents using Metabolites from Commensal Microbiome Device Hemorrhoids are enlarged or varicose veins of the tissues at the anus or rectal outlet. They are the most frequent cause of rectal bleeding. Anal and perianal pruritus, soreness and excoriation occur commonly in patient suffering from hemorrhoids, fistulas and proctitis. Careful local toilet practices with attention to any minor, fecal soiling, adjustment of the diet to avoid hard stools, the use of bulk forming materials such as bran and a high residue diet are helpful. Soothing preparations containing mild astringents such as bismuth subgallate, Zinc oxide, Peru balsam and hamamelis with lubricants, vasoconstrictors or mild antiseptics, in the form of topical ointments, creams and suppositories, are used to provide symptomatic relief. Local anesthetics may be included to relieve pain, and corticosteroids may be used when infection is not present; preparations containing either group of drugs are intended only for short-term use after exclusion of infections, such as herpes simplex; prolonged use can cause atrophy of the anal skin. Bismuth Subgallate Compound (Bismuth Subgallate+Bismuth Oxide+Peru Balsam+Zinc Oxide)

Ointment, 2.25%+0.87%+1.875%+10.75%

Suppository, 59 mg+24 mg+49 mg+296 mg+400 mg commensal microbiota metabolites.

Indications:—To relieve anal and perianal pain, itching and soreness associated with hemorrhoids, anal fissures. To reduce anal inflammation in the absence of infection.

Example 7

Personalized Microbiome Repository and Re-use for Various Treatments

The seed-microbiota of a person is acquired from birth and co-evolves with the host and it becomes and integral modulator of several key metabolic processes. When you are in the best health, your microbiota is also best adapted and optimized for your bodily needs and metabolism. Although there are general similarities among human microbiota, each person's microbiota is highly unique and co-adapted with the host cells with respect to binding nature, gut adaptability to diet, colonizing capacity and functional microbiome-metabolome. As you age or as your metabolism changes, or succumb to disease conditions, the commensal microbiota signature also changes, sometimes a good change otherwise not so. It is ideal to have a microbiota bank for each person to catalogue their microbiota and to monitor the health status of their microbiota. Further, they can also source their own microbiota for future medical and diagnostic applications. The temporal changes and diversity indexes in microbiome can help to predict various health metabolic conditions such as diabetes, obesity, chronic inflammation and atheroscelorsis.

Microbiome/microbiota banking services provide the banking as a long-term proactive health care service for personalized health and well-being. Proprietary technologies were developed to expand and make 'humanized designer' version of a person's microbiota based on different parameters such as dietary changes, health supplement-adapted, and other medications adapted (NSAIDS, painkillers etc.). Further, the strength in microbiome is leveraged to design new microbiome therapeutics for various disease conditions and indications.

Microbiome/microbiota banking helps people to catalogue their-own microbiome or microbiota on a yearly basis. The bank keeps track of the microbiota changes based on various parameters and sequence information (quantitative and qualitative diversity, gene diversity, ratio of Bacteriodetes, proteobacteria, Firmicute ratio (BPF ratio) over time. Based on this analysis, dietary and health-care preventative interventions can be recommended and reported to a primary care physician. The members have the option to expand and re-infuse their microbiota as additional service. Healthcare providers are consulted to enhance the quality of life based on microbiota science. Further, the members can also opt to expand and donate their microbiome for members or close relatives of their family. BiomSafe allows you to store your microbiome at various time-intervals and use it later for re-infusing for any health or indications. Save and store your highly health-promoting microbiome when you are in superior health.

Benefits:

Store your microbiome annually (2-5 times based on level of service)

Track the temporal microbiome changes and recommend dietary and health-care preventative interventions Can co-relate your health data with your microbiome data and predict the best health promoting microbiome Expand the best microbiome using the disclosed system and methods technology and create designer microbiome which can be re-infused for any health or indications Donate their microbiome for members or close relatives of their family Example 8

Studying the Role of Bacteriophages in Human Gut and for Culturing Specific Humanized Gut-bacteria Optimized Bacteriophages A growing body of evidence suggests that healthy gut function early in life plays a significant role in adult well-being. Chronic malnutrition and chronic or repeated gut infection have been implicated in the development of environmental enteropathy, which in turn has been implicated in the development of stunting. This condition, generally characterized by a reduced linear growth rate, is disproportionally prevalent in developing countries, and is associated with numerous pathologies including lack of response to oral vaccines, cognitive impairment, metabolic diseases, and trans-generational perinatal morbidity.

Precise engineering of the gut microbiome requires understanding of host-microbiome interactions, including population dynamics, mechanistic insight into nutrient use and signaling, the progression of disease, and the stability of such a complex ecosystem with respect to disruption. Such studies can be enabled by the development of a tool that would allow the specific perturbation of native microbiome communities in newborns and infants. These challenges are even more critical when considering treatment, which requires specific yet robust (e.g., resistant to resistance) perturbations to the system while at the same time having limited or no negative impact on the host.

Bacteriophage-based strategies may address many of the challenges above, as they are pathogen-specific and do not directly interact with eukaryotic cells. Furthermore, there may be ways to mitigate the development of bacterial resistance to introduced bacteriophage to the extent that an intervention could be plausible. Yet the majority of research aimed at developing bacteriophage therapeutics ceased with the advent of modern antibiotics.

The disclosed systems and methods can be used for the production of humanized designer phages that are adapted to the human gut microbiome dynamics. By co-culturing phages and various microbiota in the disclosed systems and methods one can study the real-time dynamics of microbial symbiosis in the human gut. Further how phage specifically shape microbiota and microbiome diversity can also be elucidated. Specific phages such as engineer bacteriophage that produce an antimicrobial compound that helps avoid bacteria such as enteroaggregative *Escherichia coli* or *Klebsiella* that are developing resistance to the phage, thereby increasing their value for treating associated childhood diseases. These humanized specific phage populations could be valuable for treating intestinal diseases that cause severe morbidity and mortality in developing countries as they can selectively destroy pathogenic bacteria. However, some bacteria rapidly develop resistance to the phage, which renders them useless. By inducing phage-infected bacteria to also release a toxic substance (bacteriocin), this would destroy any potentially resistant neighboring bacteria.

Food pathogens are a leading cause of death in children under five years old in the developing world but there are no effective vaccines due in part to the many different forms of the bacterium. The effects of the specific phages on the human gut microbes and its dynamics are evaluated both by sequencing to determine the quantities and types of bacteria in the gut, and by analyzing protein production in the bacteria and the mice, which will also reveal insight into the host immune response. By using the disclosed systems and methods one can develop a bacteriophage to destroy the diarrhea-causing bacterium Shigella or *Salmonella* or *Listeria* monocytogenes, and study its effect on microbial populations in the gut. How a unique phage-based editing of the gut microbiome and its functionality can be mimicked in the disclosed systems and methods. Further the disclosed systems and methods can be used for creating designer humanized phage-edited gut microbiota for various applications.

Example 9

Humanized Microbiome for Xenobiotic Metabolism

The disclosed systems and methods can be used for studying the effects of various xenobiotics and its effect on the human microbiome and thereby to the human body. Specific xenobiotic situations can be re-created by infusing various drugs and the changes in the metabolomic, proteomic, metatranscriptomics, and metagenomic studies on the gut microbiome can be specifically elucidated.

The gut microbiota is a significant component of first-pass metabolism. Prior to entering systemic circulation and reaching the target tissue, orally ingested compounds are subject to metabolism in the intestine and liver, which decreases the eventual systemic drug concentration. The gut microbiota may metabolize compounds prior to absorption, after efflux from the intestinal epithelium or following biliary excretion from the liver.

Mechanisms that link the gut microbiota and xenobiotic metabolism:

The gut microbiota can directly metabolize xenobiotics into active, inactive or toxic metabolites.

Xenobiotics may also shape the composition of the gut microbiota through antimicrobial activity or selective growth.

The gut microbiota can indirectly influence xenobiotics through the modulation of host pathways that are responsible for metabolism and transport.

This can be mediated by microbial metabolites or through the microbial modification of host metabolites.

Xenobiotics include antibiotics, therapeutics drugs, diet-derived bioactive molecules, and pollutants. In the following section, we will focus on the effects of the most described xenobiotics: antibiotics and host-targeted therapeutic drugs.

Antibiotics: antibiotics rapidly decrease overall and intraspecies bacterial diversity in the gut, increase bacterial damage and modify gene expression profiles and can promote the expansion of antibiotic-resistant strains. Most importantly, the effects of antibiotics are highly specific to the individual and can change with repeated exposures. In addition, resilience of the gut microbiota to therapeutic doses of antibiotic is also variable, with various bacterial taxa recovering to different extents and at different rates. For example, a 7-day triple therapy with clarithromycin, metronidazole, and omeprazole (commonly prescribed for *Helicobacter pylori* infections) reduced the abundance of Actinobacteria and members of the *Clostridium* and *Bifidobacteria* genera, a reduction that was still visible by sequencing after 4 years. A more recent study indicates a reproducible effect of a cephalosporin antibiotic on the less abundant members of the gut microbiota, which is dependent on the initial diversity of the community. However, more research is warranted to determine if the effects of other classes of antibiotics are similarly dependent on the initial composition of the gut microbiota.

Exposure of the gut microbiome to antibiotics has other less obvious deleterious health consequences. There is accumulating evidence in mouse models that early exposure to antibiotics promotes weight gain and several correlations have been found between antibiotic usage and the development of obesity and chronic diseases in children. Recently, researcher mimicked the pediatric usage of amoxicillin and tyrosine in mice, which significantly affected both the murine hosts (accelerated total mass and bone growth of the pups) and their gut microbiome (modifications in diversity, community structure, and gene content). Although these alterations were dependent on the number of courses and class of antibiotics used, antibiotic exposure consistently delayed the maturation of the gut microbiota. As detailed by the authors, such early-life exposure to antibiotics can have long-lasting consequences, including type 2 diabetes, kidney stones through disrupted intestinal oxalate metabolism, and altered carbohydrate profiles in the gut. However, most importantly, this study suggests that there exists a critical window of opportunity in which the gut microbiota would be particularly vulnerable to antibiotic disruption. Going forward, it will be necessary to characterize the causal relationships between these changes in the gut microbiota, antibiotics exposure, and the development of these physiological changes in mice and children. In addition, there is increasing evidence that antibiotics contribute to the loss of colonization resistance of the gut microbiota to opportunistic pathogens, such as *C. difficile,* and members of the Enterobacteriaceae family (*E. coli, Salmonella enterica,* and *Klebsiella pneumoniae*). Indeed, they can disrupt the network of interactions between members of the gut microbiota, cause the loss of bacterial ligands needed for adequate activation of the immune system, and alter the gut microbiome metabolite profiles (reducing the production of SCFAs). The exact underlying mechanisms are only beginning to be unraveled and will undoubtedly modify how and when to provide antibiotic treatments.

Researchers are still in the early stages of investigating the direct links between host-targeted drugs and the gut microbiome, but these interactions broadly consist of the enzymatic activation or inactivation of the compound. For example, SN-38, a topoisomerase I inhibitor and the active form of the chemotherapeutic drug irinotecan (also known as CPT-11), gets inactivated by the liver to SN-38-G. In this glucoronated and inactive form, it enters the gut lumen where the gut microbiota reactivates it back to the toxic and active SN-38 form through microbial beta glucuronidase activity. This microbial activation causes significant adverse side effects, such as severe diarrhea, weight loss, and suppression of the immune system, which all limit further increases in dosage.

The gut microbiota can also indirectly reduce the host's capacity to metabolize therapeutic drugs, thereby altering treatment outcomes. The liver detoxifies the widely used painkiller acetaminophen through O-sulfonation conjugation. However, a microbial metabolite, p-cresol, competes with acetaminophen for the hepatic sulfonation enzymes, leading to liver disease and failure. The pre-dose urinary concentration of p-cresol was associated with the severity of acetaminophen hepatic toxicity. As the enzymes involved have a broad substrate range beyond acetaminophen, further work combining metagenomics and metabolomics in animal models must be done to identify other drug deconjugation pathways that could also be influenced by bacterial metabolism. In contrast, microbial metabolism can be essential for successful therapeutic outcomes, especially in anticancer immunotherapies. Both cyclophosphamide and a CpG oligodeoxynucleotide-based immunotherapy required a healthy gut microbiota for their therapeutic activity.

Microbial metabolism can be essential for successful therapeutic outcomes, especially in anticancer immunotherapies. Both cyclophosphamide and a CpG oligodeoxynucleotide-based immunotherapy required a healthy gut microbiota for their therapeutic activity. Results suggested that yet unidentified members of the gut microbiota could modulate host immune responses, either via T-cell or interleukin-10 and tumor necrosis factor-a regulation. Since then, other studies have explored the immuno-modulatory effects of the gut microbiota, identifying *B. thetaiotaomicron* and *B. fragilis* to be essential for the efficacy of the antibody Ipilimumab to target the immune checkpoint blocker CTLA-4.

Example 10

Creating a Humanized Microbiome for Increased Human Longevity

The disclosed systems and methods can be used for creating a humanized microbiome for increased human longevity. The study of the extreme limits of human lifespan may allow a better understanding of how human beings can escape, delay, or survive the most frequent age-related causes of morbidity, a peculiarity shown by long-living individuals. Longevity is a complex trait in which genetics, environment, and stochasticity concur to determine the chance to reach 100 or more years of age. Because of its impact on human metabolism and immunology, the gut microbiome has been proposed as a possible determinant of healthy aging. Indeed, the preservation of host-microbes homeostasis can counteract inflammation, intestinal permeability, and decline in bone and cognitive health. Aiming at deepening our knowledge on the relationship between the gut microbiota and a long-living host, we provide for the first time the phylogenetic microbiota analysis of semi-supercentenarians, i.e., 105-109 years old, in comparison to adults, elderly, and centenarians, thus reconstructing the longest available human microbiota trajectory along aging. We highlighted the presence of a coremicrobiota of highly occurring, symbiotic bacterial taxa (mostly belonging to the dominant Ruminococcaceae, Lachnospiraceae, and Bacteroidaceae families), with a cumulative abundance decreasing along with age. Aging is characterized by an increasing abundance of subdominant species, as well as a rearrangement in their co-occurrence network. These features are maintained in longevity and extreme longevity, but peculiarities emerged, especially in semi-supercentenarians, describing changes that, even accommodating opportunistic and allochthonous bacteria, might possibly support health maintenance during aging, such as an enrichment and/or higher prevalence of health-associated groups (e.g., *Akkermansia, Bifidobacterium,* and Christensenellaceae). Probiotics have been shown to be effective in restoring the microbiota changes of older subjects, promoting different aspects of health in elderly people as improving immune function and reducing inflammation. Whether modulation of GI microbiota composition, with multi-targeted interventions, could have an effect on the prevention of frailty remains to be further investigated in the perspective of improving the health status of frail 'high risk' older individuals.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A method comprising:
   screening a first sample of gut microbiota obtained from a subject to detect and remove ova, parasites, or viruses;
   determining a first set of relative proportions and identities of the microbiota in the first sample;
   culturing the first sample to expand specific populations of microbiota in the presence of a spatial gradient of dissolved oxygen; and
   storing the expanded culture from the first sample, wherein the expanded culture comprises 20%-25% butyrate producers, 15-20% short chain fatty acid producers, 10-12% mucin degrading organisms, 1-5% mucin producers, 10-15% digestive enzyme producers, 0.5-1.0% neuro-endocrine peptide producers, 2-5% secondary bile acid metabolizers, 1-2% polyphenol and isothiocyanate producers, 5% tight junction protein production inducers, and 0.5-4% histone deacetylase producers and DNA methylase producers.

2. The method of claim 1, wherein culturing the first sample comprises:
   culturing the first sample within a cartridge, wherein the cartridge is in fluid communication with a anaerobic, ex vivo culture network comprising a nutrient medium and coated with a matrix for promoting adhesion of gut microbiota.

3. The method of claim 2, wherein the matrix comprises at least one of cell extracts, adhesion proteins, mucus, and commensal colonizing factors.

4. The method of claim 1, wherein determining the first set of relative proportions and identities of the microbiota in the first sample comprises sequencing the first sample.

5. The method of claim 1, further comprising:
   administering the expanded first sample to a human subject.

6. The method of claim 1, further comprising:
   determining a second set of relative proportions and identities of microbes from a second sample from the subject; and
   comparing the second set of relative proportions and identities to the first set of relative proportions and identities to determine temporal microbiome changes.

7. The method of claim 6, further comprising:
   recommending dietary or health-care preventative interventions based on the temporal microbiome changes.

8. The method of claim 1, wherein storing the expanded first sample comprises cryopreserving the first sample.

9. The method of claim 8, wherein storing the expanded first sample comprises maintaining the first sample at between −80° C. and −176° C.

10. The method of claim 1, wherein screening comprises removing endotoxins or pathogenic microbes.

11. The method of claim 1, wherein screening comprises performing stool culture tests.

12. The method of claim 1, wherein screening comprises testing for *Salmonella, Shigella, Escherichia coli*, O157:H7, *Yersinia enterocolitica, Campylobacter, Clostridium difficile* toxins A and B, the *Cryptosporidium* antigen, or the *Giardia* antigen.

13. The method of claim 1, wherein culturing the first sample further comprises selecting microbiota that can produce functional bioactive molecules.

14. The method of claim 13, wherein the functional bioactive molecules are selected from the group comprising consisting of bone morphogenetic protein (BMP), erythropoietin (EPO), granulocyte colony stimulating factor (G-CSF), granulocyte macrophage colony stimulating factor (GM-CSF), interleukin 2, interleukin 11, and mammary-associated serum amyloid protein (M-SAA).

15. The method of claim 13, wherein the functional bioactive molecules are complex glycosylated protein metabolites selected from the group consisting of IL-2, hematopoietic growth factors, interferons, and EGF.

* * * * *

SEQUENCE LISTING

```
<160> NUMBER OF SEQ ID NOS: 1

<210> SEQ ID NO 1
<211> LENGTH: 42
<212> TYPE: PRT
<213> ORGANISM: homo sapiens

<400> SEQUENCE: 1

Gln Gly Trp Leu Thr Phe Leu Lys Ala Ala Gly Gln Gly Thr Lys Asp
1               5                   10                  15

Met Trp Lys Ala Tyr Ser Asp Met Lys Glu Ala Asn Tyr Lys Lys Phe
            20                  25                  30

Arg Gln Ile Leu Pro Cys Leu Gly Glu Leu
            35                  40
```